United States Patent [19]

Fujioka et al.

[11] Patent Number: 4,544,775
[45] Date of Patent: Oct. 1, 1985

[54] ETHER CARBINOLS, PROCESS FOR PREPARING SAME, PRODUCTS PRODUCED ACCORDING TO SAID PROCESSES CONTAINING SAID ETHER CARBINOLS, ORGANOLEPTIC USES THEREOF, ETHER CARBOXALDEHYDES AND ORGANOLEPTIC USES THEREOF

[75] Inventors: Futoshi Fujioka, Wanamassa; Richard M. Boden, Ocean; William L. Schreiber, Jackson, all of N.J.

[73] Assignee: International Flavors & Fragrances Inc., New York, N.Y.

[21] Appl. No.: 644,059

[22] Filed: Aug. 24, 1984

Related U.S. Application Data

[60] Division of Ser. No. 574,150, Jan. 26, 1984, , which is a continuation-in-part of Ser. No. 533,915, Sep. 19, 1983, , which is a continuation-in-part of Ser. No. 507,292, Aug. 1, 1983, abandoned.

[51] Int. Cl.$^4$ .......................... C07C 43/15; A61K 7/46; C11B 9/00
[52] U.S. Cl. ................................ 568/675; 252/522 R; 568/442; 568/496; 568/665; 568/448; 568/654; 426/534; 131/276
[58] Field of Search .......................................... 568/675

[56] References Cited

FOREIGN PATENT DOCUMENTS 913919 12/1962 United Kingdom ................ 568/625

OTHER PUBLICATIONS

Wolthuis, C.A. 73 (1970) 3625a.

*Primary Examiner*—Howard T. Mars
*Attorney, Agent, or Firm*—Arthur L. Liberman

[57] ABSTRACT

Described are ether carbinols defined according to the generic structure:

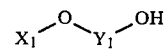

wherein $X_1$ represents a moiety selected from the group consisting of:

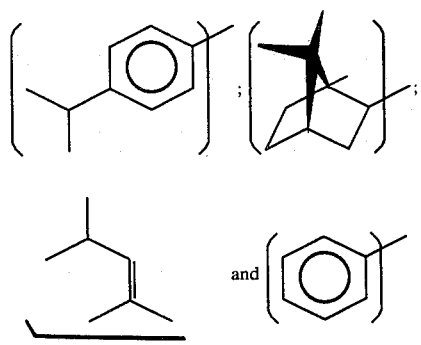

and wherein $Y_1$ represents $C_4$ or $C_5$ alkylene; $C_4$ or $C_5$ alkenylene or $C_4$ or $C_5$ alkynylene; processes for preparing such ether carbinols by means of first reacting allyl ethers with a mixture of carbon monoxide and hydrogen by means of an oxo reaction to produce ether carboxaldehydes and then reducing the thus formed ether carboxaldehydes to ether carbinols; or reacting camphene with appropriate diols; as well as methods for augmenting or enhancing the aroma or taste of consumable materials including perfumes, colognes and perfumed articles; foodstuffs, chewing gums, chewing tobaccos, medicinal products and toothpastes; and smoking tobaccos and smoking tobacco articles by adding thereto an aroma or taste augmenting or enhancing quantity of the thus produced ether carbinols.

Also described are two ether carboxaldehydes having one of the structures:

(Abstract continued on next page.)

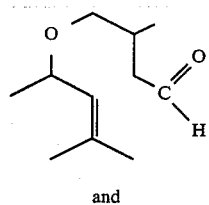

and

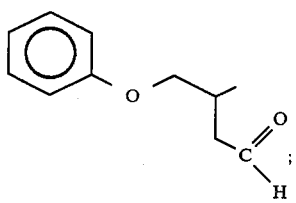

processes for preparing such ether carboxaldehydes by means of reacting out an appropriate allyl ether with a mixture of carbon monoxide and hydrogen by means of an oxo-reaction as well as methods for augmenting or enhancing the aroma or taste of consumable materials including perfumes, colognes and perfumed articles; foodstuffs, chewing gums, chewing tobaccos, medicinal products and toothpastes; smoking tobaccos and smoking tobacco articles by adding thereto an aroma or taste augmenting or enhancing quantity of the thus produced ether carboxaldehydes.

1 Claim, 26 Drawing Figures

GLC PROFILE FOR FRACTION 4 OF EXAMPLE I.

NMR SPECTRUM FOR FRACTION 4 OF EXAMPLE I, PEAK "10" OF FIG. 1

GLC PROFILE FOR EXAMPLE II. CRUDE

GLC PROFILE FOR EXAMPLE I, FRACTION 5.

NMR SPECTRUM FOR PEAK 50 OF FIG.3(B), EXAMPLE II.

GLC PROFILE FOR BULKED FRACTIONS 2-4.
1ST DISTILLATION OF EXAMPLE III.

GLC PROFILE FOR FRACTION 5 OF EXAMPLE III.

NMR SPECTRUM FOR EXAMPLE III.

GLC PROFILE FOR EXAMPLE IV.

GLC PROFILE FOR EXAMPLE IV.

NMR SPECTRUM FOR EXAMPLE IV.

IR SPECTRUM FOR EXAMPLE IV.

GLC PROFILE FOR EXAMPLE V.
CRUDE

GLC PROFILE FOR EXAMPLE VI.
CRUDE

NMR SPECTRUM FOR FRACTION 4 OF EXAMPLE V.

NMR SPECTRUM FOR FRACTION 2 OF EXAMPLE VI.

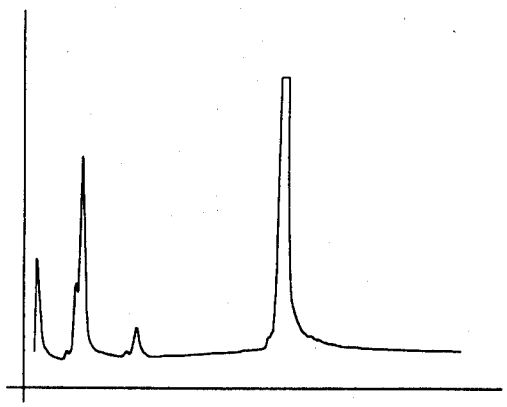
GLC PROFILE FOR EXAMPLE VII. CRUDE
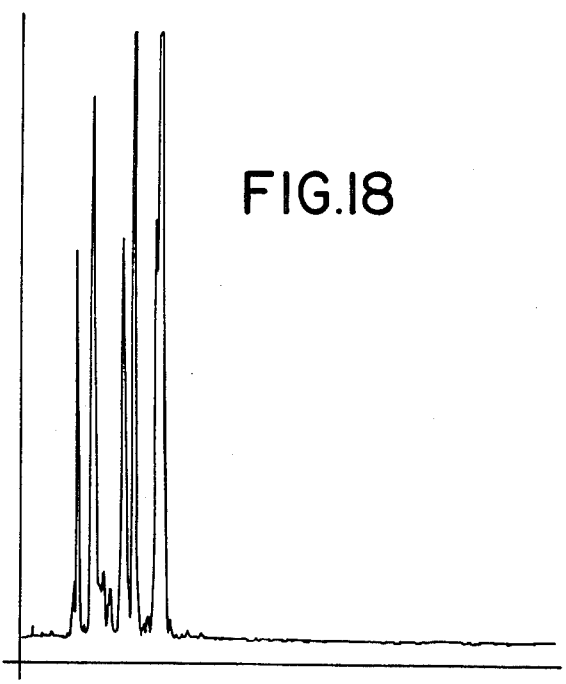
GLC PROFILE FOR FRACTION 4 OF EXAMPLE VIII, CRUDE.
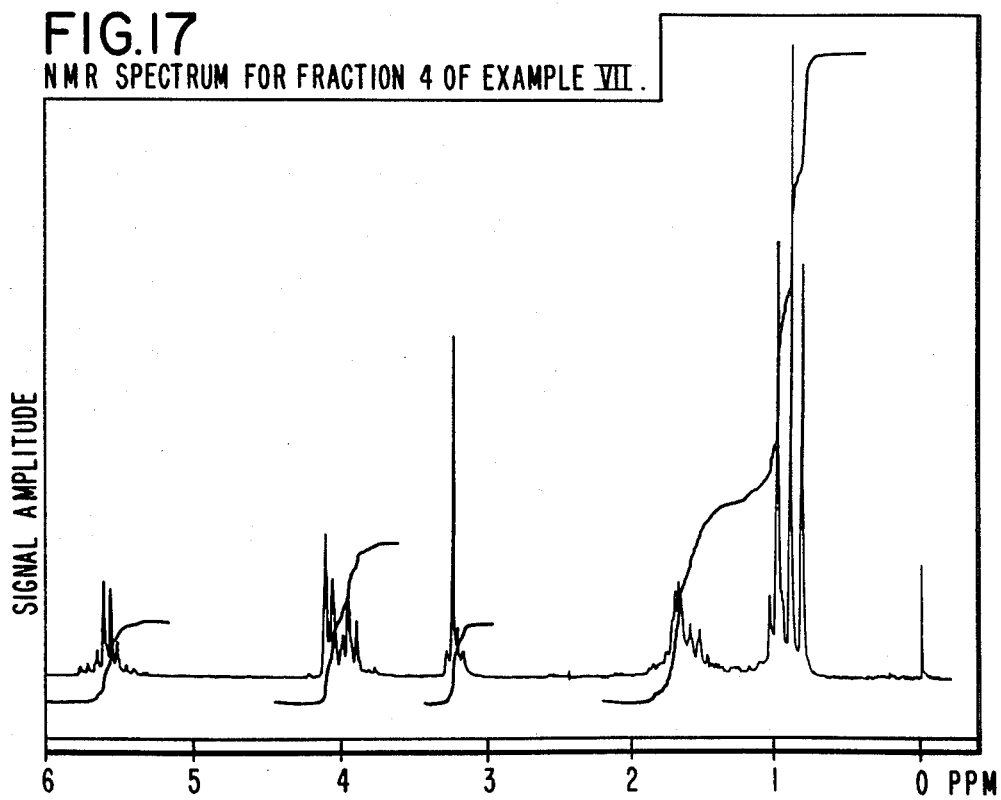
FIG.17
NMR SPECTRUM FOR FRACTION 4 OF EXAMPLE VII.

NMR SPECTRUM FOR FRACTION 8 OF EXAMPLE VIII.

GLC PROFILE FOR EXAMPLE IX.
CRUDE

GLC PROFILE FOR EXAMPLE X.
CRUDE

NMR SPECTRUM FOR FRACTION 4 OF EXAMPLE IX.

NMR SPECTRUM FOR EXAMPLE X.

ETHER CARBINOLS, PROCESS FOR PREPARING SAME, PRODUCTS PRODUCED ACCORDING TO SAID PROCESSES CONTAINING SAID ETHER CARBINOLS, ORGANOLEPTIC USES THEREOF, ETHER CARBOXALDEHYDES AND ORGANOLEPTIC USES THEREOF

This is a divisional of application Ser. No. 574,150, filed 1/26/84 which, in turn, is a continuation-in-part application of U.S. patent Ser. No. 533,915 filed 9/19/83, which, in turn, is a continuation-in-part appl. of U.S. patent Ser. No. 507,292 filed 8/1/83, now abandoned.

BACKGROUND OF THE INVENTION

The instant invention provides ether carbinols defined according to the generic structure:

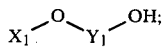

wherein $X_1$ represents a moiety selected from the group consisting of:

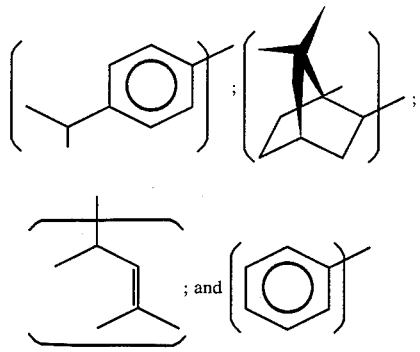

and wherein $Y_1$ represents $C_4$ or $C_5$ alkylene; $C_4$ or $C_5$ alkenylene or $C_4$ or $C_5$ alkynylene and in addition two ether carboxaldehydes defined according to the structures:

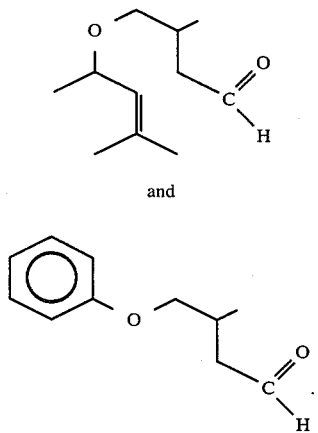

Inexpensive chemical compositions of matter which can provide nutty, woody, ozoney, fresh air dried clothing-like, green, orange, minty, patchouli-like, incense-like, oniony, garlic, lavender-like, herbaceous, leafy, pepper-like, spicy, camphoraceous, woody, floral, sweet fruity and chamomile-like aromas with patchouli-like, cedarwood, oniony, animalic sweaty, herbaceous, peppery, olibanum-like, diffusive amber, rosey and caramellic undertones are highly desirable in the art of perfumery. Many of the natural materials which provide such fragrances and contribute desired nuances to perfumery compositions as well as perfumed articles including solid or liquid anionic, cationic, nonionic or zwitterionic detergents, perfumed polymers, fabric softener compositions, fabric softener articles, hair preparations, cosmetic powders and the like are high in cost, vary in quality from one batch to another and/or are generally subject to the usual variations of natural products.

By the same token, materials which can provide nutty, patchouli-like, oriental, incense, musky, sandalwood, walnut-like, onion, garlic, floral, and fruity aromas and tastes are highly useful and are well known in the art of flavorings for foodstuffs, toothpastes, chewing gums, medicinal products and chewing tobaccos. Many of the natural materials which provide such flavor nuances and contribute desired nuances to flavors and compositions are high in cost, vary in quality from one batch to another and/or are generally subject to the usual variations of natural products.

Materials which can provide woody, incense-like, oriental and patchouli aroma and taste nuances to smoking tobacco compositions and components of smoking tobacco articles prior to and on smoking in the main stream and in the side stream are highly desirable in the smoking tobacco art. Many of the natural materials which provide such flavor and aroma nuances and contribute desired nuances to flavoring compositions for smoking tobacco and smoking tobacco article components, e.g., filters and wrappers as well as the main body of the tobacco, are high in cost, vary in quality from one batch to another and/or are generally subject to the usual variations of natural products.

There is, accordingly, a continuing effort to find synthetic materials which will replace, enhance or augment the essential flavor and fragrance notes provided by natural essential oils or compositions containing the same. Unfortunately, many of the synthetic materials either have the desired nuances only to a relatively small degree, or else contribute undesirable or unwanted odor to the compositions. The search for materials which provide, for example, a more refined fresh orange flavor or a more refined peppermint flavor (for use in oral hygiene flavors, e.g., mouthwashes) for example, has been difficult and relatively costly in the areas of both natural products and synthetic products. By the same token, the search for materials which can provide a more refined patchouli aroma or a more refined "fresh air" aroma, for example, has been difficult and relatively costly in the areas of both natural products and synthetic products.

Artificial flavoring agents for foodstuffs have received increasing attention in many years. For many years, such foods flavoring agents have been preferred over natural flavoring agents at least, in part, due to their diminished cost and their reproducible flavor qualities. For example, natural food flavoring agents such as extracts, concentrates and the like are often subject to wide variations due to changes in quality, and type and treatment of the raw materials. Such variations can be reflected in the end product and result in unfavorable flavor characteristics in said end product. Additionally, the presence of the natural product in the ultimate food may be undesirable because of increased tendency to spoil. This is particularly troublesome in food and food uses where such products as dips, soups, chips, sausages, gravies and desserts and the like are apt to be stored prior to use.

The fundamental problem in creating artificial flavoring agents is that the artificial flavor to be achieved be as natural as possible. This generally proves to be a difficult task since the mechanism for flavor development in many foods, medicinal products, chewing gums, toothpastes and chewing tobaccos is not completely known. This is noticable in products having fresh orange and peppermint flavor characteristics particularly.

Even more desirable are products that conserve to substitute for difficult to obtain natural perfumery oils and at the same time substitute for natural flavoring ingredients in foodstuffs, chewing gums, medicinal products, toothpastes, chewing tobaccos, smoking tobaccos and smoking tobacco article components.

Oxo reaction products are well known in the art of perfumery. Thus, U.S. Pat. No. 4,374,277 issued on Feb. 15, 1983, the specification of which is incorporated by reference herein, describes branched chain $C_{11}$ aldehydes and alcohols, processes for producing same by (i) first dimerizing isoamylene (2-methyl-2-butene) to form a mixture of diisoamylenes and (ii) reacting the resulting mixture or separated components thereof with carbon monoxide and hydrogen by means of an oxo reaction, as well as methods for augmenting or enhancing the aroma of perfumes, colognes and perfumed articles by adding thereto aroma augmenting or enhancing quantities of the thus produced $C_{11}$ branched chain aldehydes and alcohol compositions of matter.

Furthermore, ether crboxaldehydes are well known in the art of perfumery for augmenting or enhancing the aroma of perfume compositions or perfumed articles. Thus, U.S. Pat. No. 4,359,390 issued on Nov. 16, 1982, the specification for which is incorporated by reference herein discloses the use of such ether carboxaldehydes as the compound having the structure:

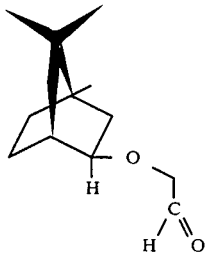

in augmenting or enhancing the aroma of perfume compositions, colognes and perfumed articles (e.g., perfume plastics, solid or liquid anionic, cationic, nonionic or zwitterionic detergents, fabric softener compositions or drier-added fabric softener articles.

Application for U.S. patent Ser. No. 335,794 filed on Sept. 26, 1983, the specification for which is incorporated by reference herein discloses 5-alkoxybicyclo[2.2.1]heptane-2-oxypropane derivatives.

The invention of Ser. No. 335,794 relates to 5-alkoxybicyclo[2.2.1]heptane-2-oxypropane derivatives defined according to the structure:

(wherein R represents $C_1$–$C_3$ alkyl and wherein Z represents one of the moieties, carbinol having the structure:

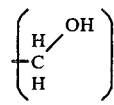

or carboxaldehyde having the structure:

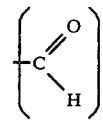

and uses thereof in augmenting or enhancing the aroma of perfume compositions, colognes or perfumed articles (e.g., solid or liquid anionic, cationic, nonionic or zwitterionic detergents, fabric softener compositions, fabric softener articles, cosmetic powders, hair preparations, perfumed polymers and the like).

In addition, U.S. Pat. No. 4,114,420 issued on Nov. 8, 1983 describes the process for the preparation of an aldehyde ether of the general formula:

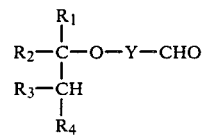

wherein $R_1$ and $R_2$ each, independently of the other, represent a $C_1$ to $C_4$ alkyl radical, and $R_3$ and $R_4$ each, independently of the other, represent a hydrogen atom or a $C_1$ to $C_3$ alkyl radical, or wherein $R_1$ represents a $C_1$ to $C_4$ alkyl radical, $R_2$ and $R_3$ together with the carbon atoms to which they are attached form a 5-membered or 6-membered cycloaliphatic ring, and $R_4$ represents a hydrogen atom or a $C_1$ to $C_3$ alkyl radical, and wherein Y represents —$CH_2$—$CH_2$—$CH_2$— or —$CH_2$—$CH(CH_3)$—, which comprises contacting a compound of the general formula:

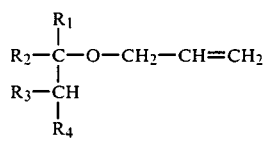

wherein $R_1$, $R_2$, $R_3$, and $R_4$ are as defined above, with hydrogen and carbon monoxide under hydroformylation conditions and in the presence of a catalytic amount of a hydroformylation catalyst.

Nothing in the prior art, however, suggests the ether carbinols or ether carboxaldehydes of our invention or the products produced according to the processes which comprise reacting allylic ethers with carbon monoxide and hydrogen via an oxo reaction to produce compositions of matter containing such ether carboxaldehydes or subsequent reduction thereof to produce the ether carbinols of our invention or the organoleptic uses of same.

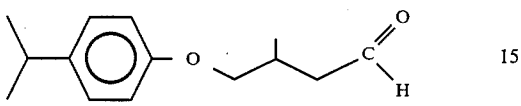

Figure 1:
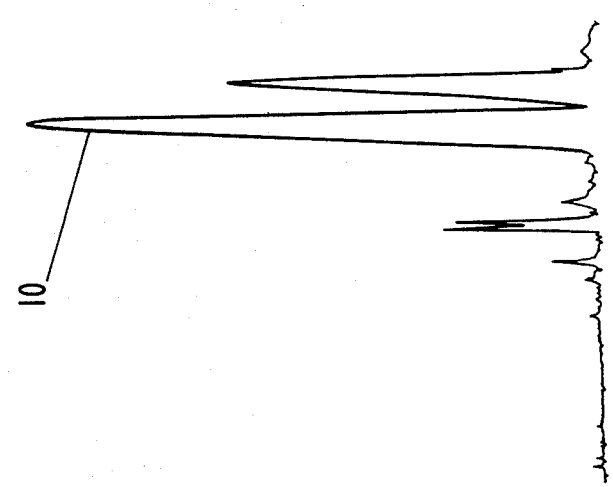
FIG. 1 is the GLC profile for fraction 4 of the distillation product of the reaction product of Example I containing the compound having the structure.
Figure 2:
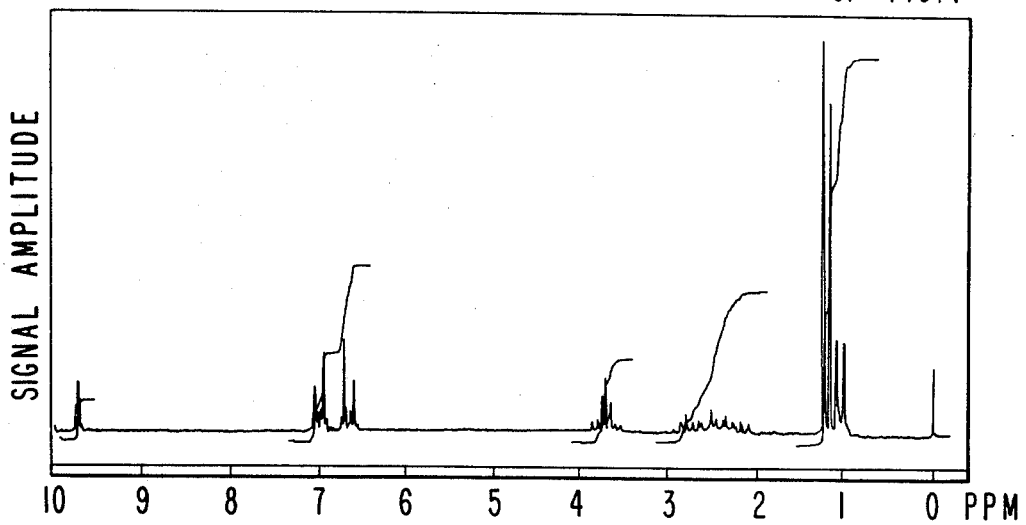

FIG. 2 is the NMR spectrum for the peak indicated by reference numeral "10" on FIG. 1 which is the GLC profile for fraction 4 of the distillation product of the reaction product of Example II containing the compound having the structure:

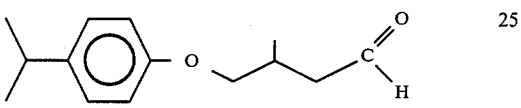

(Conditions: Field strengths: 100 MHz; solvent: CFCl$_3$).

Figure 3A:
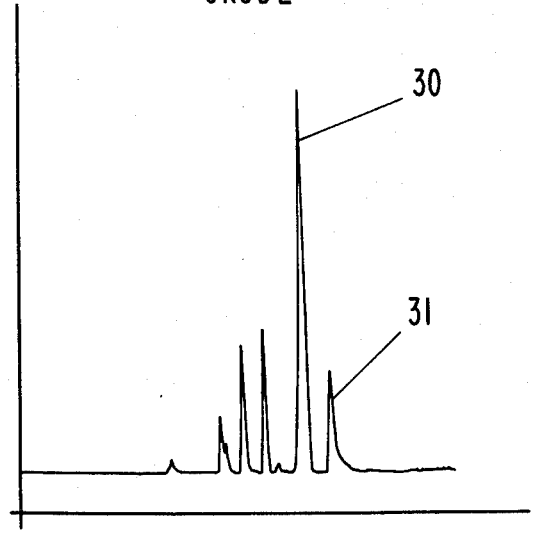

FIG. 3A is the GLC profile for the crude reaction product of Example II containing the compound having the structure:

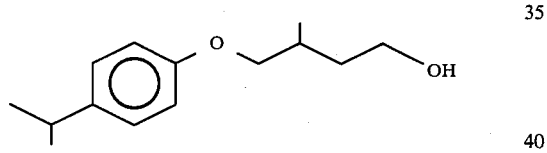

Figure 3B:
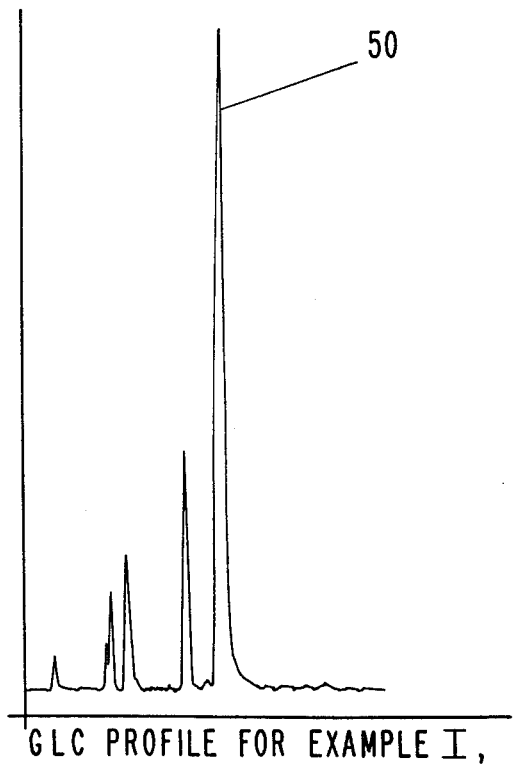

FIG. 3B is the GLC profile for fraction 5 of the distillation product of the reaction product of Example II containing the compound having the structure:

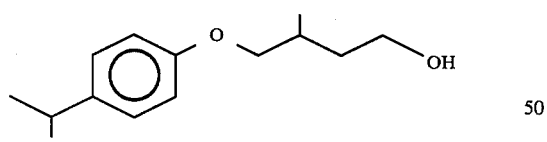

Figure 4:
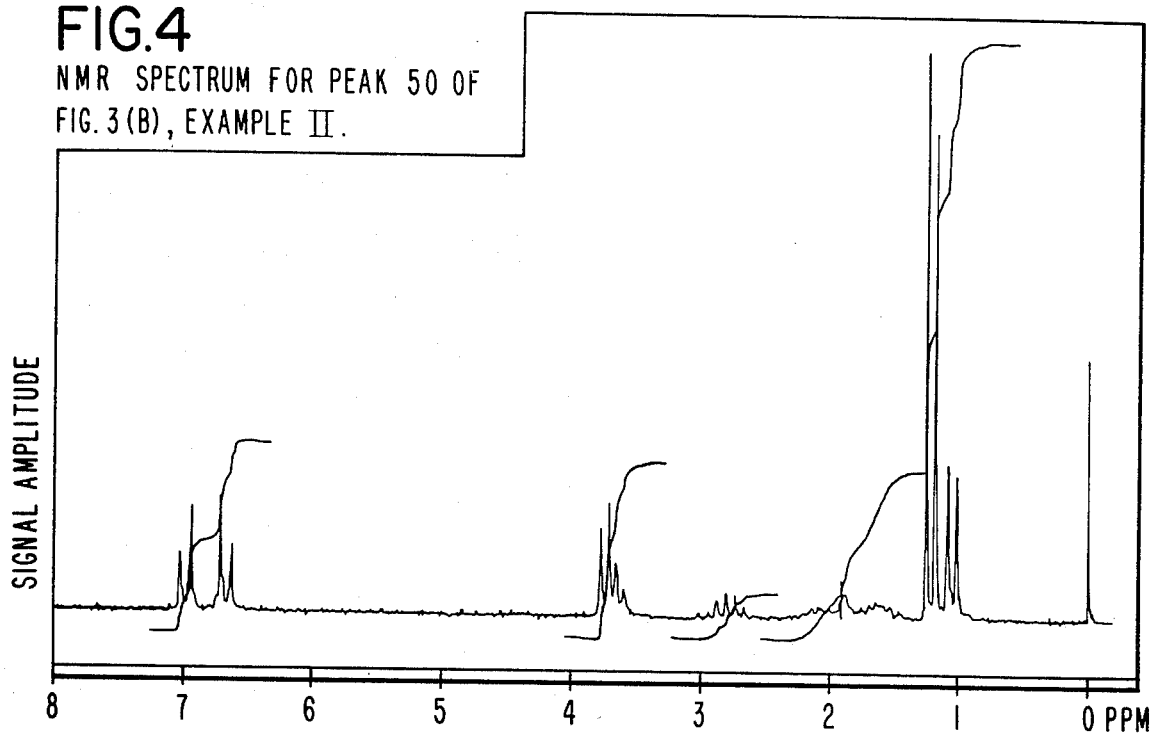

FIG. 4 is the NMR spectrum for peak "50" of the GLC profile of FIG. 3B for the compound having the structure:

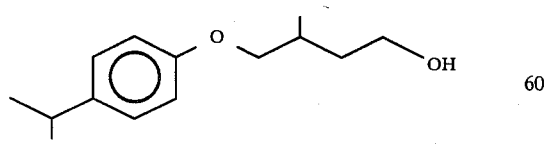

(Conditions: Field strength: 100 MHz; solvent: CFCl$_3$).

Figure 5:
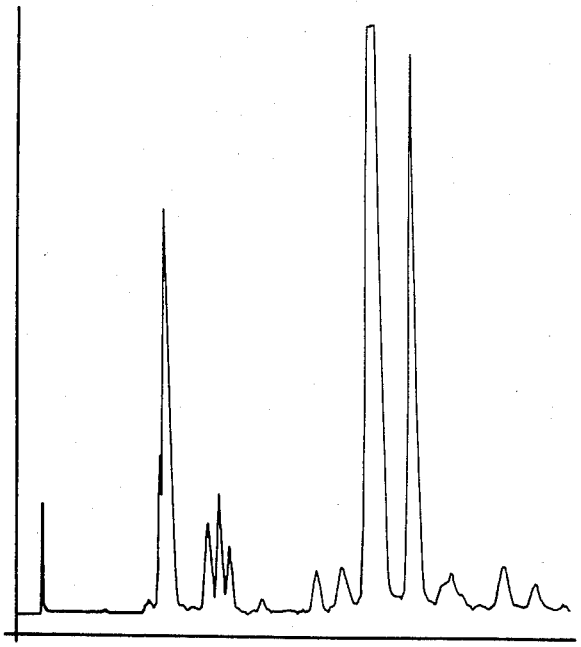

FIG. 5 is the GLC profile for bulked fractions 2-4 of the first distillation product of the reaction product of Example III containing the compound having the structure:

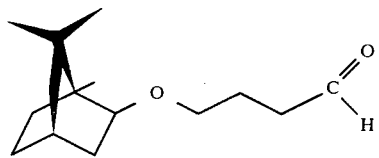

Figure 6:
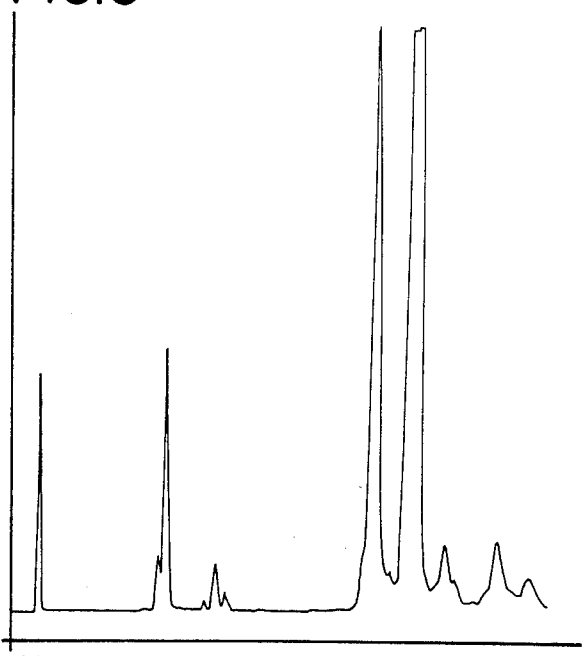

FIG. 6 is the GLC profile for fraction 5 of the second distillation product of the reaction product of Example III containing the compound having the structure:

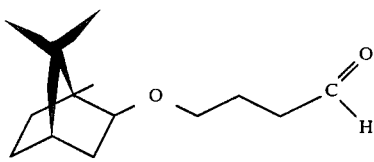

Figure 7:
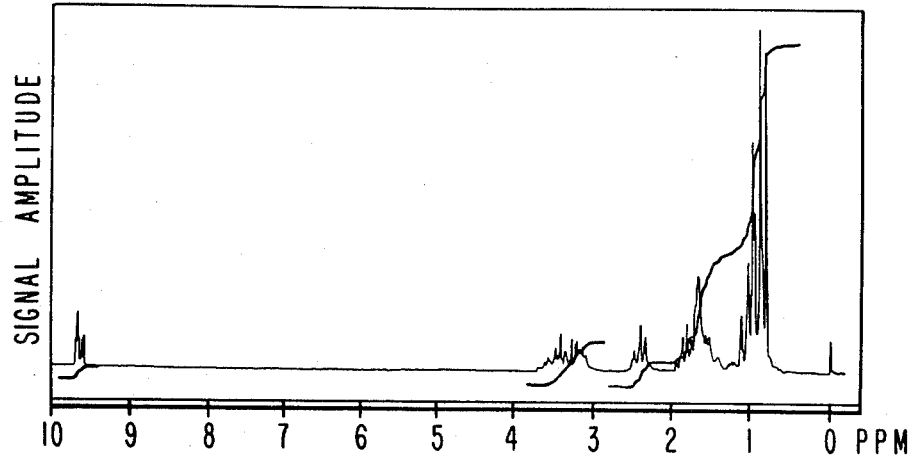

FIG. 7 is the NMR spectrum for the compound having the structure:

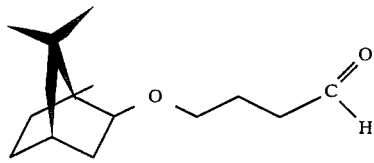

produced according to Example III (Conditions: Field strength: 100 MHz; solvent: CFCl$_3$).

Figure 8:
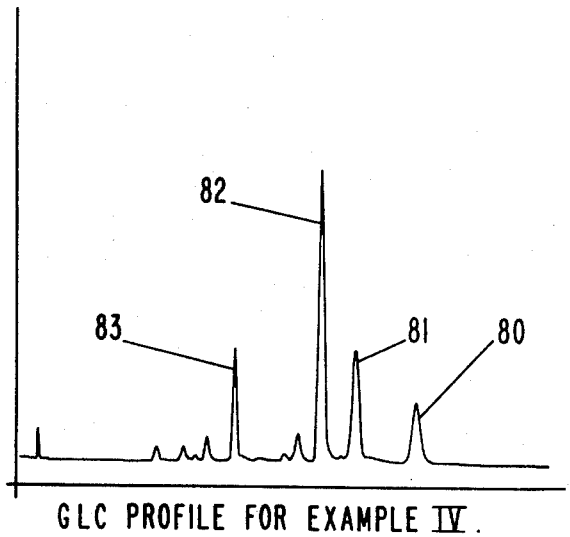

FIG. 8 is the GLC profile for the crude reaction product of Example IV containing the compounds having the structures:

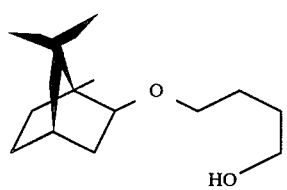

and

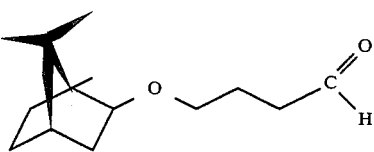

Figure 9:
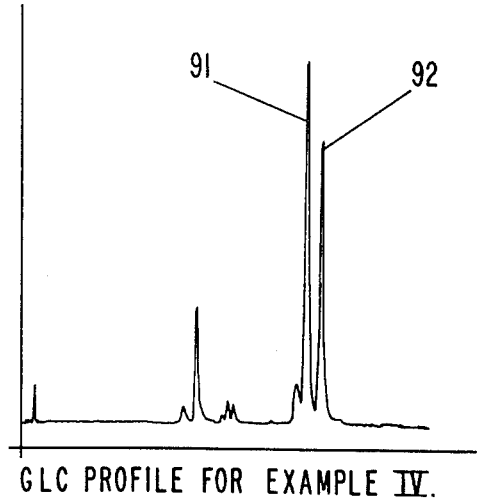

FIG. 9 is the GLC profile for fraction 2 of the distillation product of the reaction product of Example IV containing the compound having the structure:

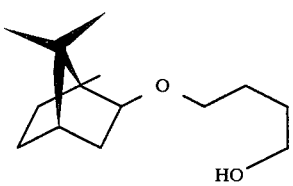

Figure 10:
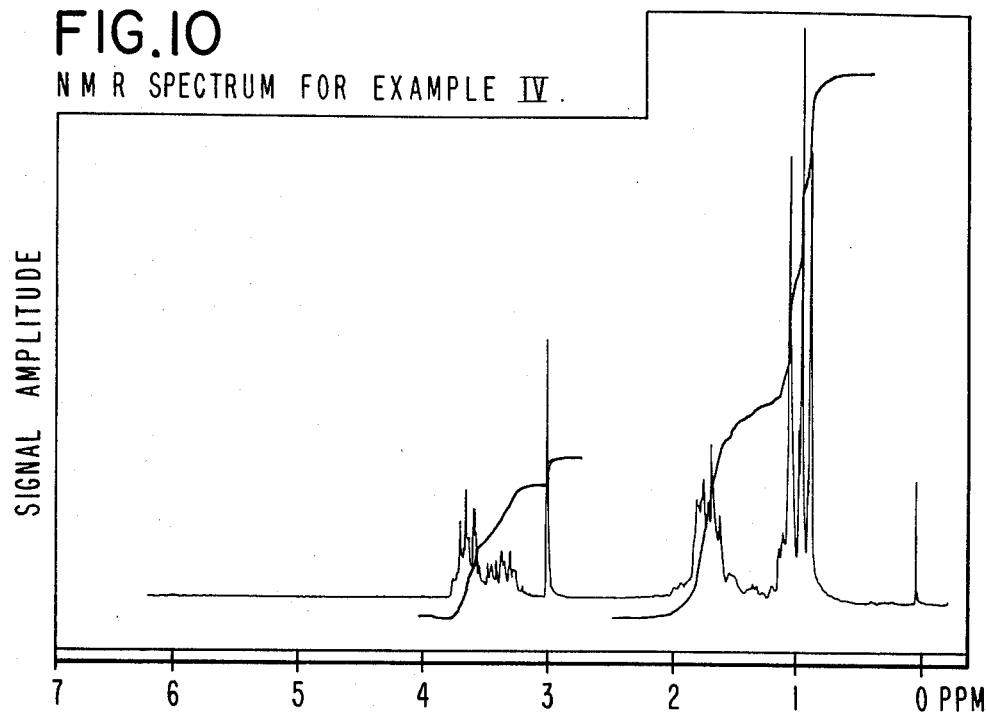

FIG. 10 is the NMR spectrum for the compound having the structure:

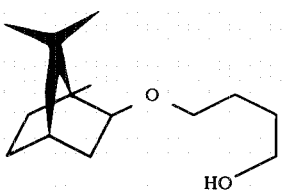

produced according to Example IV (Conditions: Field strength: 100 MHz; solvent: CFCl₃).

Figure 11:
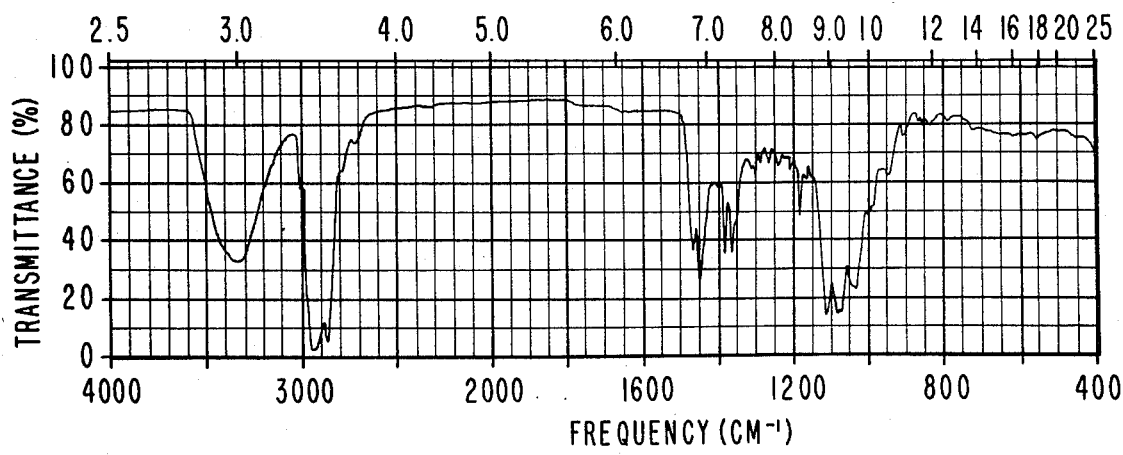

FIG. 11 is the infra-red spectrum for the compound having the structure:

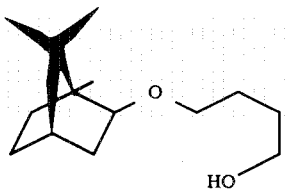

produced according to Example IV.

Figure 12:
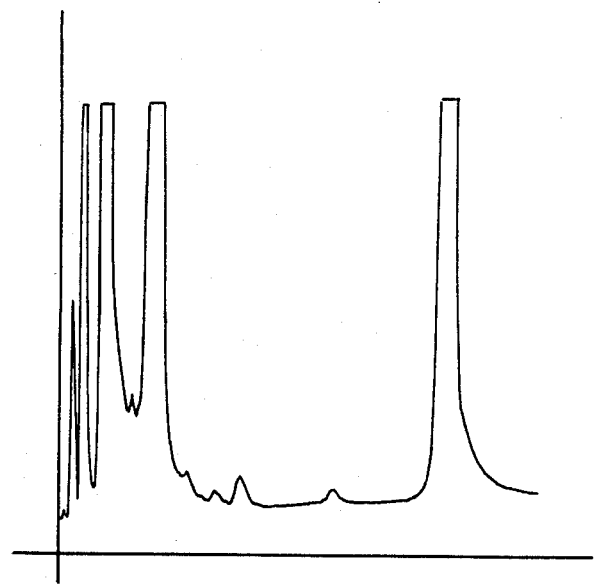

FIG. 12 is the GLC profile of the crude reaction product of Example V containing the compound having the structure:

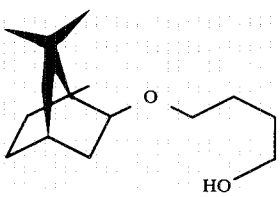

Figure 13:
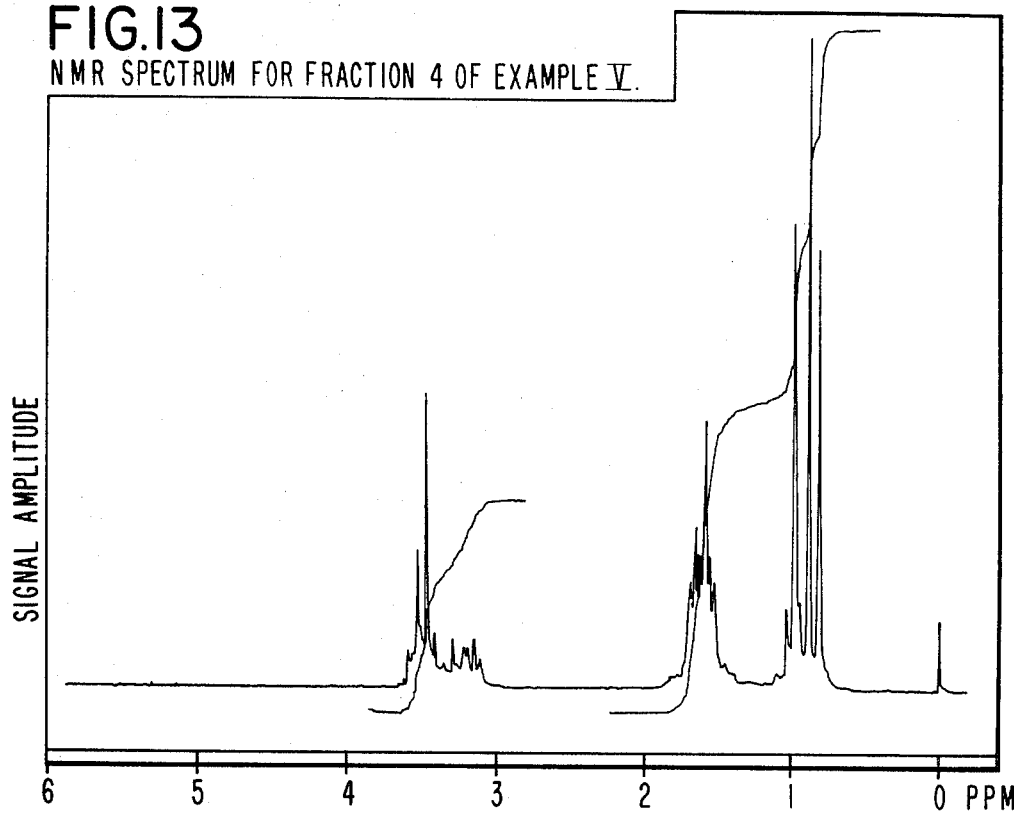

FIG. 13 is the NMR spectrum for fraction 4 of the distillation product of the reaction product of Example V containing the compound having the structure:

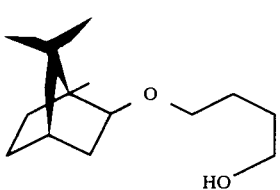

Figure 14:
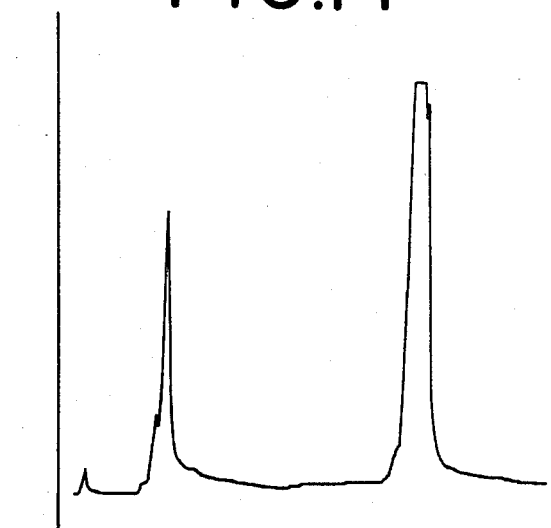

FIG. 14 is the GLC profile for the crude reaction product of Example VI containing the compound having the structure:

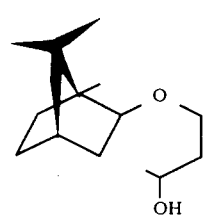

Figure 15:
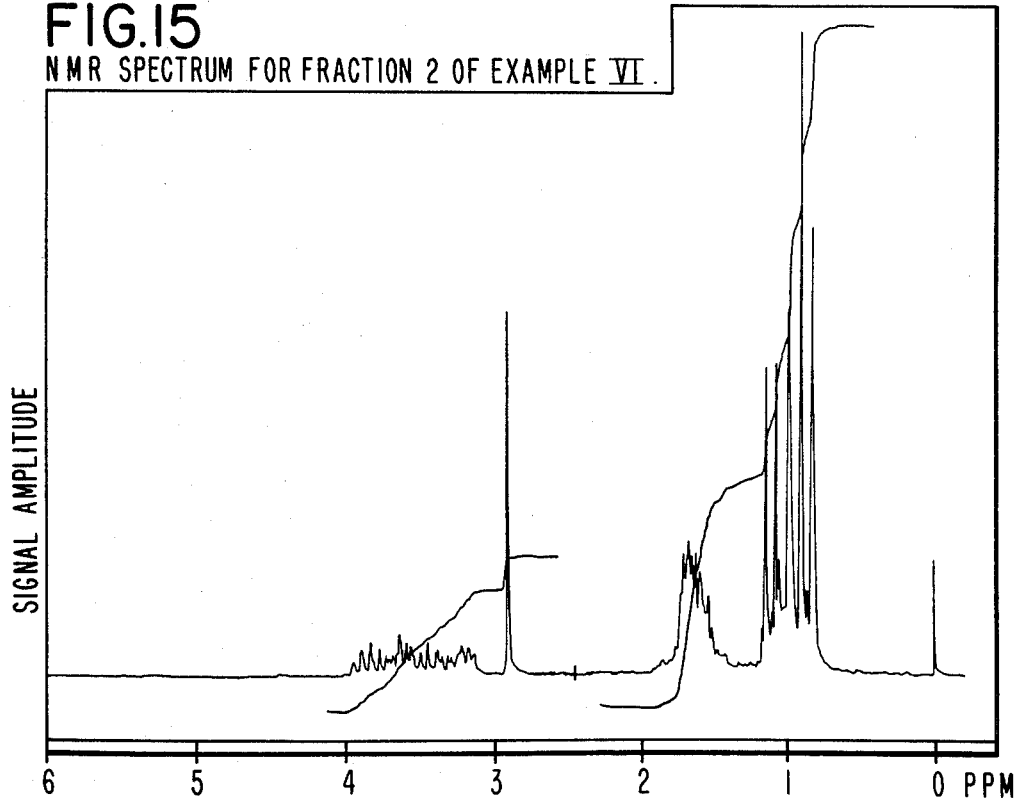

FIG. 15 is the NMR spectrum for fraction 2 of the distillation product of the reaction product of Example VI containing the compound having the structure:

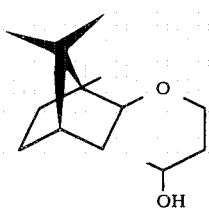

(Conditions: Field strength: 100 MHz; solvent: CFCl₃).

FIG. 16 is the GLC profile for the crude reaction product of Example VII containing the compound having the structure:

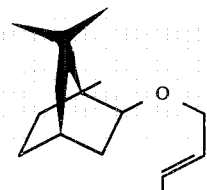

(Conditions: SE 30 column programmed at 100°–200° C. at 8° C. per minute).

FIG. 17 is the NMR spectrum for fraction 4 of the distillation product of the reaction product of Example VII containing the compound having the structure:

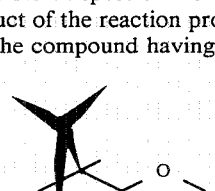

FIG. 18 is the GLC profile for fraction 4 of the distillation product of the reaction product of Example VIII containing the compound having the structure:

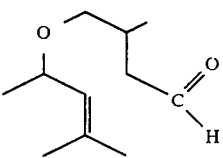

Figure 19:
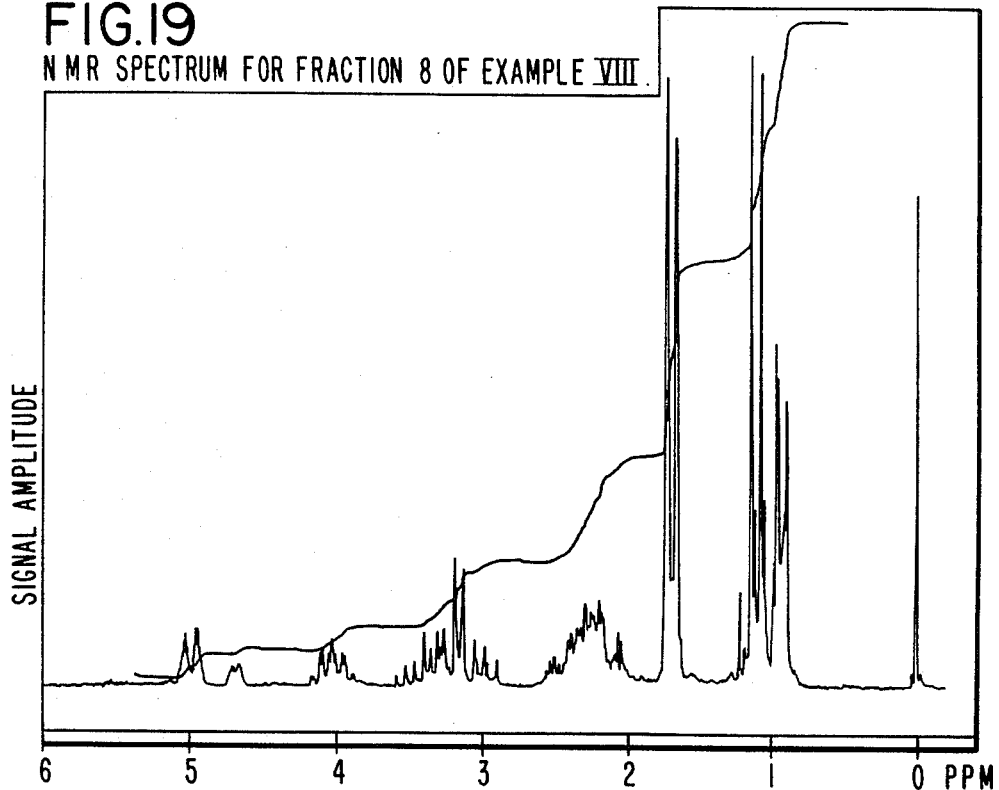

FIG. 19 is the NMR spectrum for fraction 8 of the distillation product of the reaction product of Example VIII containing the compound having the structure:

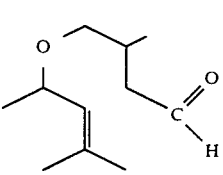

(Conditions: Field strength: 100 MHz; solvent: CFCl₃).

Figure 20:
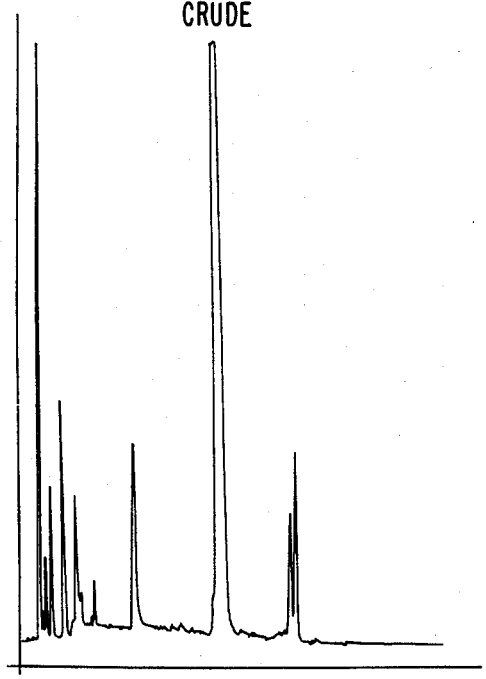

FIG. 20 is the GLC profile for the crude reaction product of Example IX containing the compound having the structure:

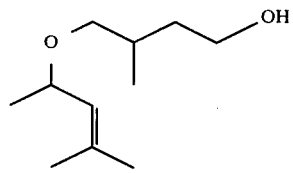

Figure 21:
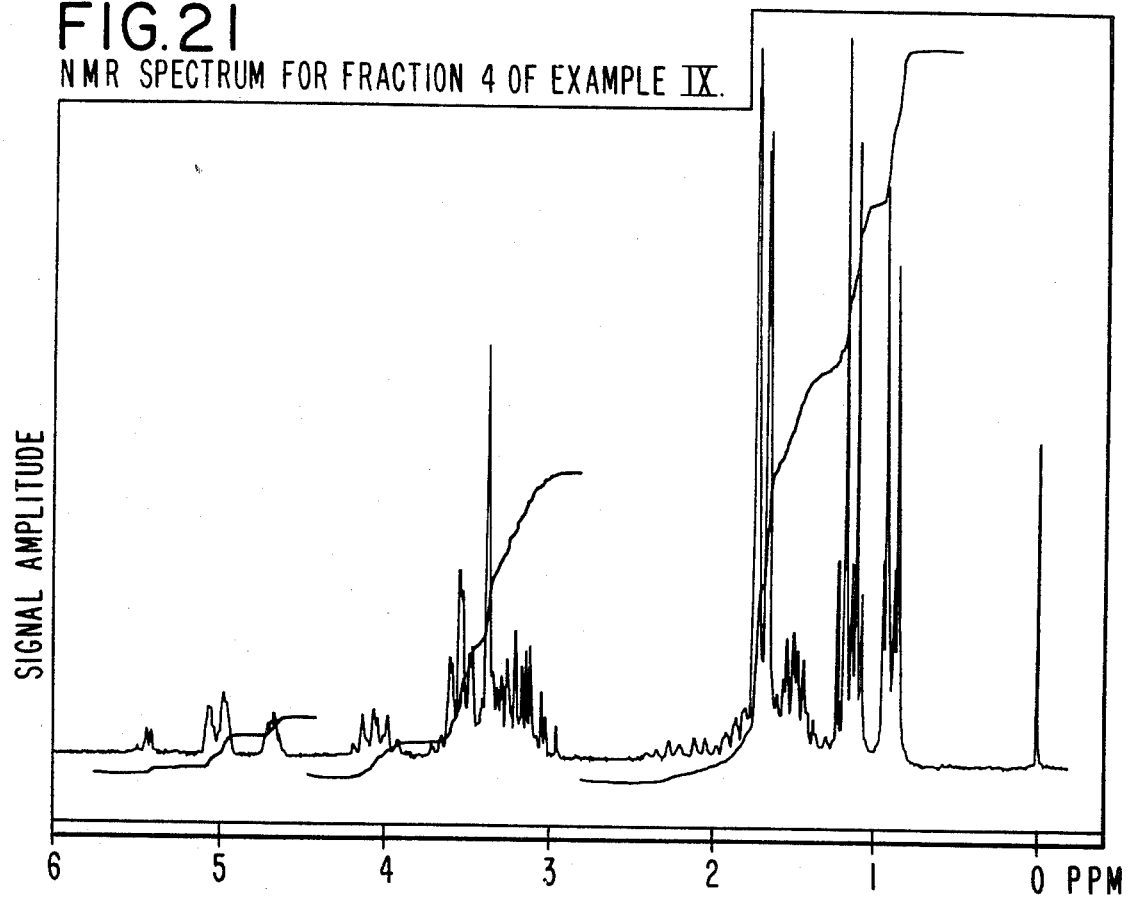

FIG. 21 is the NMR spectrum for fraction 4 of the distillation product of the reaction product of Example IX containing the compound having the structure:

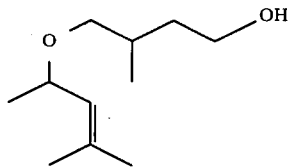

(Conditions: Field strength: 100 MHz; solvent: CFCl₃).

Figure 22A:
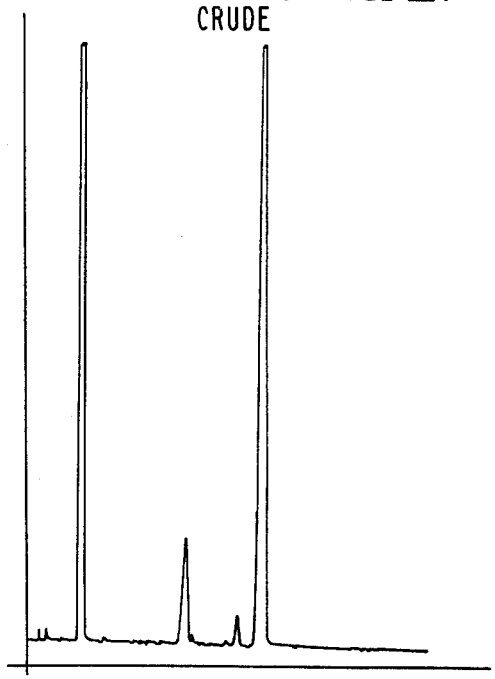

FIG. 22A is the GLC profile for the crude reaction product of Example X containing the compound having the structure:

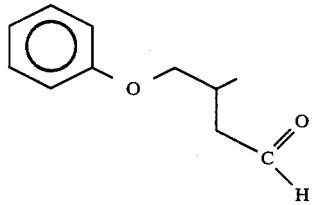

Figure 22B:
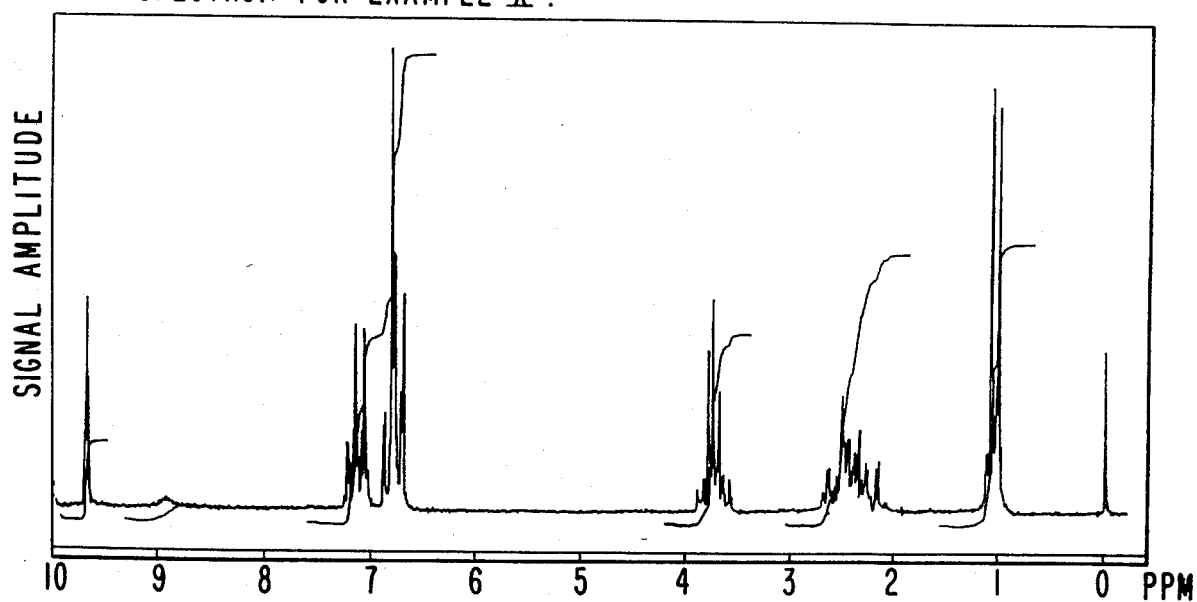

FIG. 22B is the NMR spectrum for the compound having the structure:

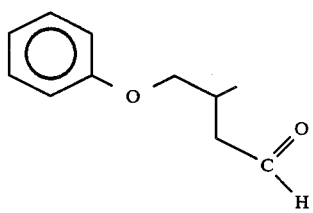

produced according to Example X (Conditions: Solvent: CFCl₃: Field strength: 100 MHz).

Figure 23:
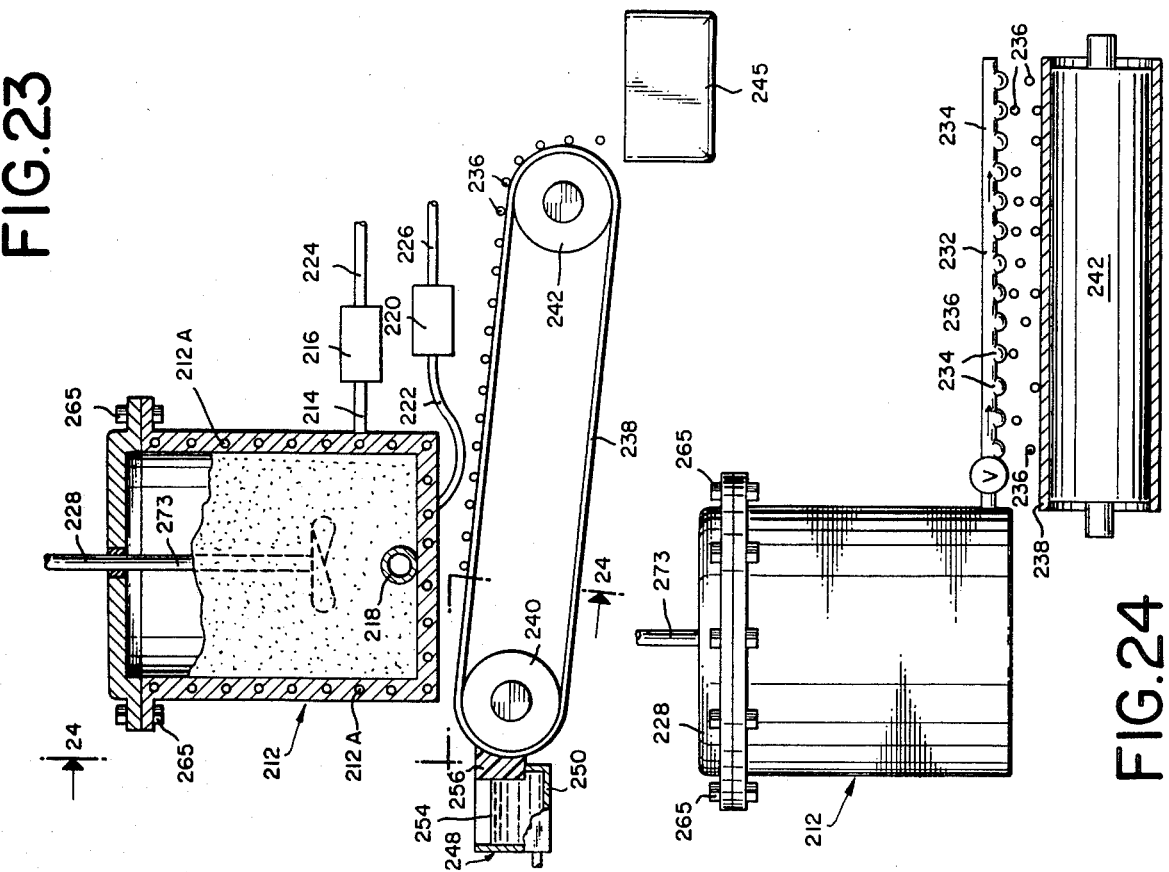

FIG. 23 represents a cut-away side elevation view of apparatus used in forming perfumed polymers which contain embedded therein at least one of the ether carbinols of our invention.

Figure 24:
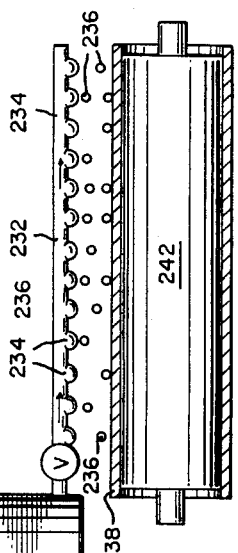

FIG. 24 is a front view of the apparatus of FIG. 23 looking in the direction of the arrows.

DETAILED DESCRIPTION OF THE DRAWINGS

FIG. 1 is the GLC profile for fraction 4 of the distillation product of the reaction product of Example I containing the compound having the structure:

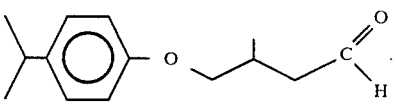

The peak indicated by the Reference 10 is the peak for the compound having the structure:

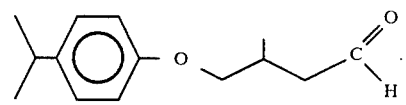

FIG. 3A is the GLC profile for the crude reaction product of Example II containing the compounds having the structures:

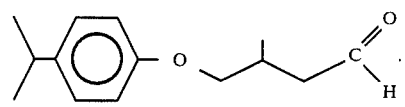

and

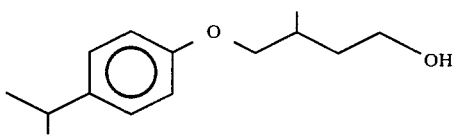

The peak indicated by Reference 30 is the peak for the compound having the structure:

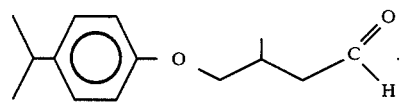

The peak indicated by Reference 31 is the peak for the compound having the structure:

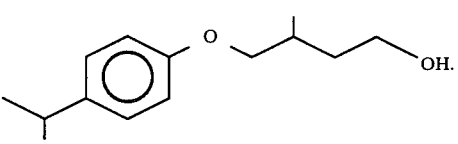

FIG. 3B is the GLC profile for fraction 5 of the distillation product of the reaction product of Example II containing the compound having the structure:

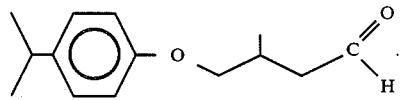

The peak indicated by Reference 50 is the peak for the compound having the structure:

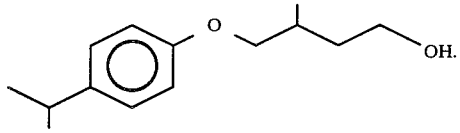

FIG. 8 is the GLC profile for the crude reaction product of example IV containing the compounds having the structures:

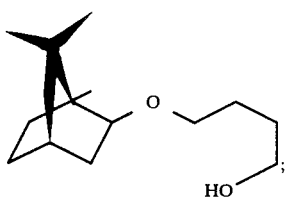

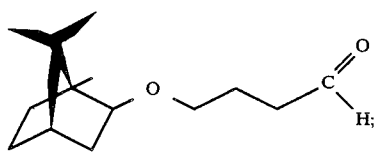

; and

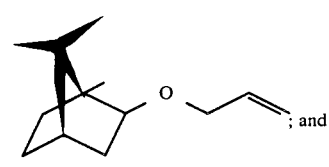

The peak indicated by Reference 80 is the peak for the compound having the structure:

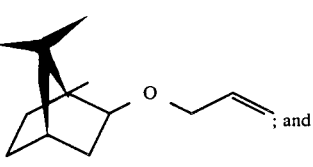

The peak indicated by Reference 81 is the peak for the compound having the structure:

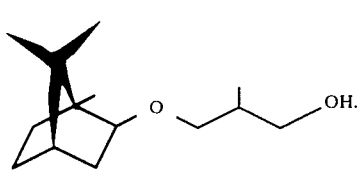

The peak indicated by Reference 82 is the peak for the compound having the structure:

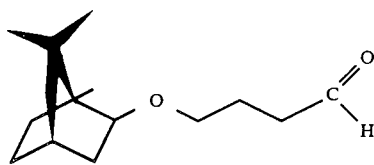

The peak indicated by Reference 83 is the peak for the compound having the structure:

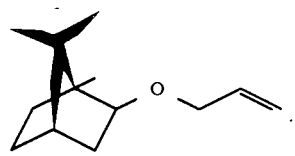

FIG. 9 is the GLC profile for fraction 2 of the distillation product of the reaction product of Example IV containing the compound having the structure:

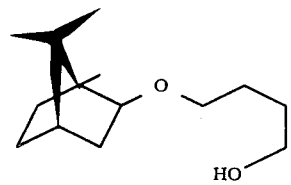

as well as the compound having the structure:

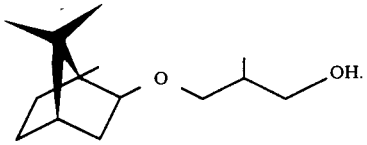

The peak indicated by Reference 91 is the peak for the compound having the structure:

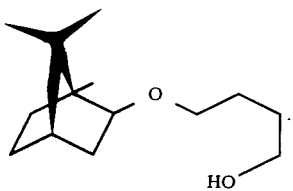

The peak indicated by Reference 92 is the peak for the compound having the structure:

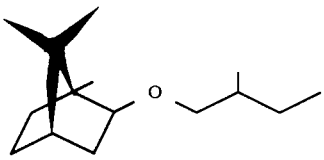

Referring to FIGS. 23 and 24, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 23 and 24, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and the perfuming substance which is at least one of the ether carbinols or ether carboxaldehydes of our invention or mixtures of ether carbinols and ether carboxaldehydes and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cyclinder 212A having heated coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90-100 sayboldt seconds. The heater 218 is operated to maintain the upper portion of the container 212 within a temperature range of, for example, 220°-270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°-270° C.

Thus, the polymer or mixture of polymers added to the container 212 is heated from 10-12 hours, whereafter the perfume composition or perfume material which contains one or more of the ether carbinols and/or ether carboxaldehydes of our invention is quickly added to the melt. Generally, about 10-45 percent by weight of the resulting mixture of the perfumery substance is added to the polymer.

After the perfume material is added to the container 212, the mixture is stirred for a few minutes, for example, 5-15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with one or more of the ether carbinols and/or ether carboxaldehydes of our invention or mixture of perfume substances and one or more of the ether carbinols and/or ether carboxaldehydes of our invention, will continuously drop through the orifices 234 downwardly from the conduit 232. During this time, the temperature of the polymer intimately admixed with the perfumery substance in the container 212 is accurately controlled so that a temperature in the range of from about 240°-250° C., for example, (in the case of low density polyethylene) will exist in the conduit 232. The regulation of the temperature through the controls 216 and 220 is essential in order to insure temperature balance to provide for the continuous dripping or dropping of molten polymer intimately admixed with the perfume substance which is all of or which contains one or more of the ether carbinols and/or ether carboxaldehydes of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of other functional products, e.g., garbage bags and the like.

THE INVENTION

The present invention provides ether carbinols defined according to the generic structure:

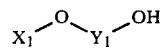

wherein $X_1$ represents a moiety selected from the group consisting of:

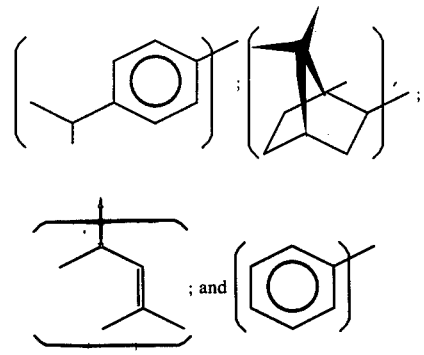

and wherein $Y_1$ represents $C_4$ or $C_5$ alkylene; $C_4$ or $C_5$ alkenylene or $C_4$ or $C_5$ alkynylene as well as ether carboxaldehydes defined according to one of the following two structures:

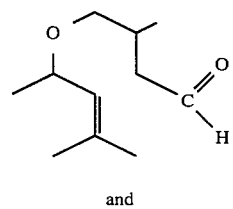

and

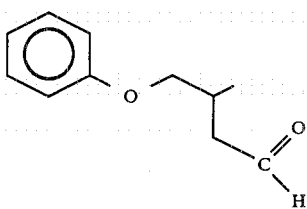

The present invention also provides processes for preparing such compounds by means of carrying out an oxo reaction on an appropriate allyl ether using carbon monoxide and hydrogen and either isolating the resulting carboxaldehyde or further reducing the resulting ether carboxaldehyde to form the appropriate ether carbinol; or reacting camphene with either an alkylene diol, an alkenylene diol or an alkynylene diol in the presence of an appropriate catalyst to form a norbornyloxycarbinol. More specifically, an allyl ether defined according to the formula:

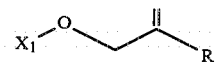

is reacted with a mixture of carbon monoxide and hydrogen using an oxo reaction catalyst whereby a mixture of aldehydes is formed defined according to the structure:

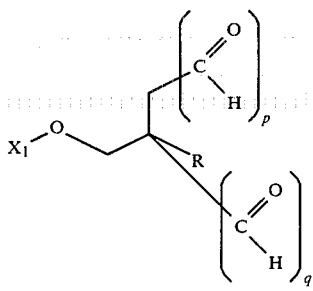

according to the reaction:

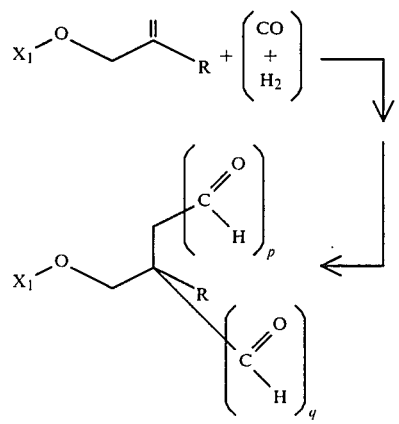

wherein p and q each represent 0 or 1 with the proviso that when p is 0 q is 1 and that when p is 1 q is 0 and wherein R represents hydrogen or methyl. The resulting ether carboxaldehyde mixture defined according to the structure:

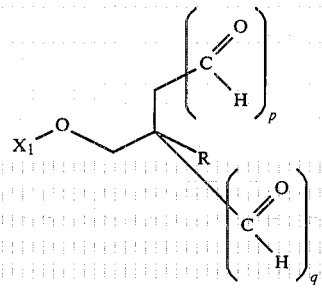

may be used "as-is" for its organoleptic properties or may be further reduced with an appropriate reducing agent to form the ether carbinol defined according to the structure:

on the other hand, another process of our invention involves the reaction of camphene defined according to the structure:

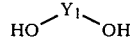

with an alkylene diol, an alkenylene diol or an alkynylene diol defined according to the structure:

$$HO{-}Y_1{-}OH$$

in order to form a norbornyloxycarbinol defined according to the structure:

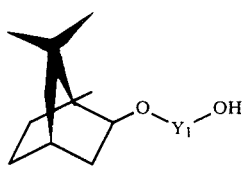

according to the reaction:

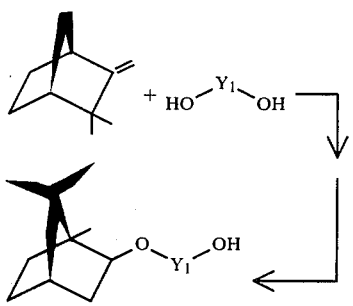

wherein $Y_1$ represents $C_4$ or $C_5$ alkylene; $C_4$ or $C_5$ alkenylene; or $C_4$ or $C_5$ alkynylene.

The present invention also provides products produced according to such processes. The resulting compounds, ether carboxaldehydes of our invention or ether carbinols of our invention, produced according to the processes of our invention are capable of augmenting or enhancing the aroma and/or taste of consumable materials including foodstuffs, chewing gums, toothpastes, medicinal products, chewing tobaccos, perfumes, perfumed articles, colognes, smoking tobaccos and smoking tobacco articles.

Thus, the ether carbinols and ether carboxaldehydes of our invention augment or enhance the ozoney, fresh air dried clothing-like, green, orange, nutty, woody, minty, patchouli, incense-like, oniony, garlic, lavender-like, herbaceous, leafy, pepper, spicy, camphoraceous, sweet, fruity and chamomile-like aromas and patchouli-like, cedarwood-like, oniony, animalic sweaty, herbaceous, peppery, olibanum, diffusive amber, rosey and caramellic undertones of perfumed compositions, colognes and perfumed articles (including soaps, anionic, cationic, nonionic or zwitterionic detergents, fabric softener compositions, fabric softener articles, optical brightner compositions, perfumed polymers, hair preparations and the like, thus fulfilling a need in the field of perfumery as well as detergent, cologne, fabric softener and cosmetic manufacture.

In the area of foodstuffs, chewing gums, toothpastes, medicinal products and chewing tobaccos, as well as flavoring compositions therefor, the ether carboxaldehydes and/or ether carbinols of our invention produced according to the processes of our invention in part augment or enhance green, fresh orange, patchouli, oriental, incense-like, musky, sandalwood, walnut-like, onion, garlic, floral and fruity aroma and taste nuances, thereby creating valuable aroma and taste nuances useful for oral hygiene, peppermint, fresh orange, walnut, onion, garlic and fruit flavored foodstuffs.

In smoking tobacco, smoking tobacco flavoring compositions, substitute smoking tobacco and substitute tobacco flavoring compositions, the ether carboxaldehydes and/or ether carbinols of our invention produced according to the processes of our invention in part augment and enhance woody, incense, oriental and patchouli aroma and taste nuances both prior to and on smoking in the main stream and in the side stream.

The ether carbinols of our invention defined according to the structure:

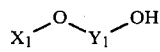

wherein $X_1$ represents a structure selected from the group consisting of:

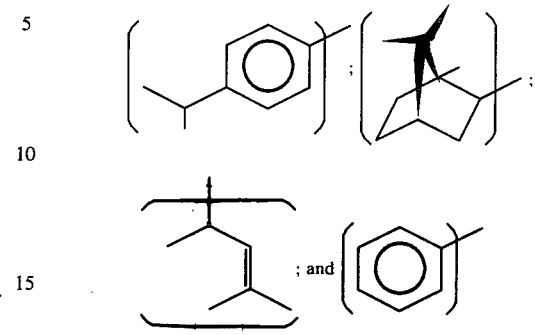

and wherein $Y_1$ represents $C_4$-$C_5$ alkylene, $C_4$-$C_5$ alkenylene and $C_4$-$C_5$ alkynylene may be prepared by means of first reacting allyl ethers defined according to the structure:

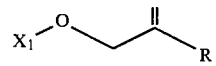

with carbon monoxide and hydrogen thereby carrying out a "oxo" reaction. The allyl ethers defined according to the structure:

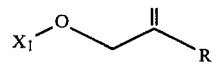

may be prepared by means of any standard ether synthesis, e.g., a "Williamson" synthesis or a synthesis as set forth in U.S. Pat. No. 4,163,068 issued on July 31, 1979, the specification for which is incorporated by reference herein. Thus, the ethers so useful in our invention may be formed by reacting an alcohol with another alcohol, for example, an allylic alcohol in the presence of an acid catalyst such as para toluene sulphonic acid at reflux conditions. The reaction mass is refluxed for a period of from two hours up to ten hours, after which period of time the reaction product is separated from the reaction mass by distillation.

The ethers so useful in practicing our invention may also be formed by reacting the corresponding alcohol with an appropriate allylic halide or other organic halide as the case may be. This reaction is carried out under the influence of base comprising the step of placing the reactants for the process and the base, respectively, in tow immiscible phases; an organic phase and either (i) an aqueous base phase or (ii) a solid base phase with the reactants being located substantially entirely in the first mentioned organic phase and the base being located substantially intirely in the second mentioned phase; and adding to the two phase system a "phase transfer agent" which may be one or more of several organic quaternary ammonium salts.

Specific examples of "phase transfer agents" useful in our invention are as follows:
Tricapryl methyl ammonium chloride;
Cetyl trimethyl ammonium bromide; and
Benzyl trimethyl ammonium hydroxide.
In general, the "phase transfer agents" most preferred have the generic formula:

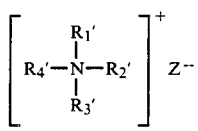

wherein at least one or $R_1'$, $R_2'$, $R_3'$ and $R_4'$ is $C_6-C_{14}$ aryl, $C_6-C_{10}$ aralkyl, $C_6-C_{20}$ alkyl, $C_6-C_{14}$ aralkyl and $C_6-C_{20}$ alkenyl, and the other of $R_2'$, $R_3'$ and $R_4'$ is alkyl such as methyl, ethyl, n-propyl, i-propyl, 1-butyl, 1-methyl-2-propyl, 1-pentyl and 1-octyl and Z- is an anion such as chloride, bromide and hydroxide.

This aspect of the process is carried out in an inexpensive solvent which is inert to the reaction system such as toluene, benzene, o-xylene, m-xylene, p-xylene, ethyl benzene, n-hexane, cyclohexane, methylene dichloride and o-dichlorobenzene.

This aspect of the process is carried out at a temperature in the range of from about 10° C. up to about 150° C. with a temperature range of 30°–120° C. being preferred. The reaction time is inversely proportional to the reaction temperature, with lower reaction temperatures giving rise to greater reaction times; and, accordingly, the reaction time ranges from about 30 minutes up to about 10 hours.

In this aspect of the process, the mole ratio of alcohol reactant to organic halide (e.g., allylic halide) is in the range of from 0.5:1.5 up to about 1.5:0.5 with a preferred ratio of alcohol to organic halide (e.g., allylic halide) being from about 1:1 up to about 1:1.2.

The mole ratio of base to alcohol in the reaction mass may be in the range of from about 0.75:1 up to about 1.5:1 with a preferred mole ratio of base:alcohol being from about 1:1 up to about 1.2:1.

The quantity of "phase transfer agent" in the reaction mass based on the amount of alcohol in the reaction mass may vary from 0.5 grams per mole of alcohol up to 25 grams of "phase transfer agent" per mole of alcohol with a preferred concentration of "phase transfer agent" being in the range of from about 2.5 up to about 7.5 grams of "phase transfer agent" per mole of alcohol.

This aspect of the process is preferably carried out at atmospheric pressure since that is the most convenient condition. However, lower or higher pressures can be used without detrimentally affecting the ultimate yield of desired product. The particular based used in the reaction is not critical, but, preferred are sodium hydroxide and potassium hydroxide.

The individual ethers which are reactants for our invention in the oxo process described, infra, can be obtained in pure form or in substantially pure form by conventional purification techniques. Thus, the products can be purified and/or isolated by means of distillation, extraction, crystallization, preparative chromatographic techniques and the like. It has been found desirable to purify the ethers by fractional distillation in vacuo.

The thus-formed ethers having the structure:

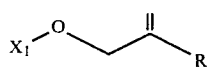

wherein R represents methyl or ethyl and $X_1$ is as defined, supra, are then reacted with a mixture of carbon monoxide and hydrogen using a particular range of temperatures and partial pressures of hydrogen and carbon monoxide over one of several alternative "oxo" type reaction catalysts over a period of various residence times.

Thus, the oxo reaction is carried out thusly:

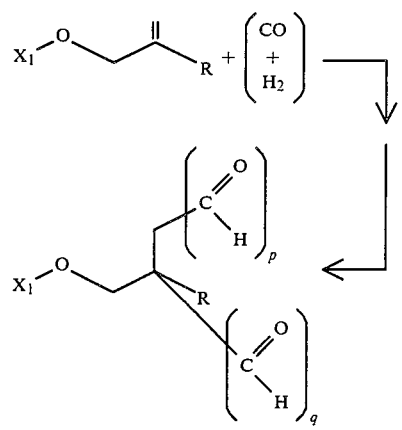

wherein $X_1$, R, p and q are defined, supra, with the production of a small amount of alcohol defined according to the structure:

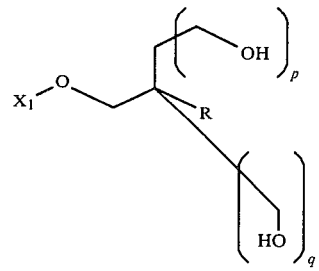

The reaction is carried out at temperatures of between 150° C. and 300° C.; at pressures of between 20 and 250 atmospheres; with the ratio of partial pressure of carbon monoxide:hydrogen being from 0.1:1 up to 1:0.1. Any oxo type reaction catalyst may be used, but most preferably, the catalyst to yield the best perfume and flavor mixtures are as follows:

Dicobalt octacarbonyl;
Cobalt octanoate;
Palladium chloride;
Rhodium trichloride;
Iron pentacarbonyl;
Nickel tetracarbonyl;
Polymer-bonded rhodium catalyst (e.g., rhodium bonded on a polystyrene substrate);
Tris-triphenyl phosphine rhodium-1-chloride;
Rhodium Aceto acetate dicarbonyl;
Rhodium Aceto acetate/triphenyl phosphine mixture.

The reaction time may vary from about two hours up to about 30 hours; and the reaction time is a function of the temperature and pressure of reaction; and the desired ratio of aldehyde:alcohol reaction product. Insofar as the instant invention is concerned, a high ratio of alcohol:aldehyde reaction product will be created by high temperature high pressure and a long period of time whereas a high ratio of aldehyde:alcohol will be created as a result of low temperature low pressure and short period of time.

At the end of the reaction, the reaction product is separated from the catalyst and unreacted materials by standard "work-up" means if desired; e.g., neutralization of catalyst; followed by extraction and fractional distillation; usually an initial fractional distillation by means of distillation through a 2-4 plate or stone packed column; followed by a more careful fractionation of the bulked center-cut fractions on, for example, a spinning band column or multiplate (14-50 plate) fractionation column.

The resultant aldehyde reaction product may then be reduced by means of using specific reducing agents according to the reaction:

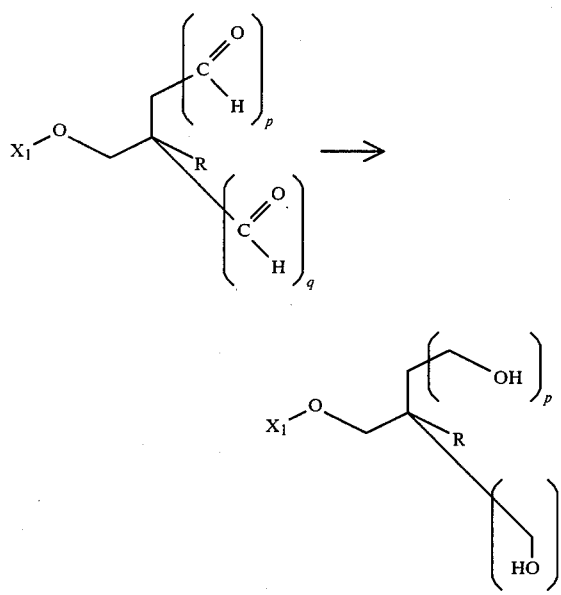

wherein $X_1$, R, p and q are defined, supra. The reduction reaction is carried out at a temperature in the range of from about 60° C. up to about 100° C. at from about one atmosphere up to about 10 atmospheres but preferably at reflux conditions for a period of time of between about one and 10 hours. The reaction takes place in the presence of a solvent which is inert to the reactants and the reaction product, such as, anhydrous isopropyl alcohol. Such solvent must be capable of being retained during the course of the reaction and not being so volatile as to boil off during the reaction. The reducing agent may be any standard aldehyde-alcohol reducing agent but preferable reducing agents are alkyl metal borohydrides, for example, sodium borohydrides, potassium borohydrides and lithium borohydrides. Other reducing agents that can be used are lithium aluminum hydride and aluminium isopropoxide and potassium isobutoxide. At the end of the reaction the reaction product which is the ether carbinol of our invention may be isolated from the reaction mass by standard isolation means, e.g., fractional crystallization, fractional distillation and commercial liquid chromotography procedures.

In addition, nornyloxocarbinols defined according to the generic structure:

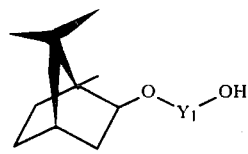

wherein $Y_1$ represents alkylenyl, alkenylenyl and alkynylenyl having from four up to five carbon atoms may be prepared by reacting camphene with a diol defined according to the structure:

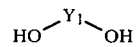

according to the reaction:

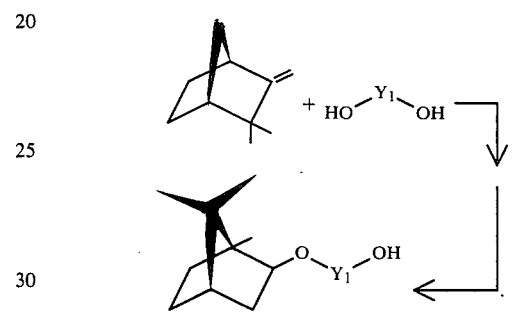

This reaction takes place in the presence of a catalyst which is a Lewis acid, for example, boron trifluoride etherate at temperatures in the range of from about 60° C. up to about 100° C. and at pressures in the range of from about 1 atmosphere up to about 10 atmospheres. Preferably, the reaction takes place at 80° C. at atmospheric pressure and at reflux condition. The reaction time may vary from about two hours up to about 20 hours depending upon the temperature of reaction. Higher temperatures of reaction gives rise to lower times of reaction and lower temperatures of reaction require higher times of reaction but a better overall yield. The mole ratio of diol having the structure:

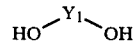

to camphene may vary from about 1:2 up to about 3:1 with a mole ratio of diol:camphene of about 2:1 being preferred. At the end of the reaction the reaction mass is neutralized and the reaction product defined according to the generic structure:

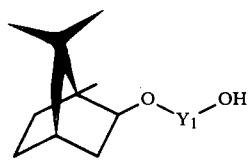

is purified for organoleptic uses as by means of fractional distillation.

Examples of ether carbinols and ether carboxaldehydes which are useful in the practice of our invention and their organoleptic properties are set forth in the following Tables I (Ether Carbinols) and II (Ether Carboxaldehydes):

TABLE I

| Ether Carbinol | Perfumery Evaluation | Food Flavor Evaluation | Tobacco Flavor Evaluation |
|---|---|---|---|
| 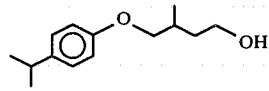<br>produced according to Example II | Nutty, woody, ozoney, fresh air dried cloth, green-orange aroma profile. | A green aroma and taste with fresh orange nuances. | |
| 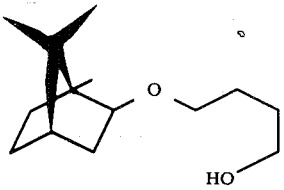<br>produced according to Examples IV or V. | A minty patchouli aroma with patchouli undertones. | A patchouli, oriental, incense, musky and sandalwood aroma and taste profile at 5 ppm causing it to be good for oral hygiene and peppermint flavor. | |
| 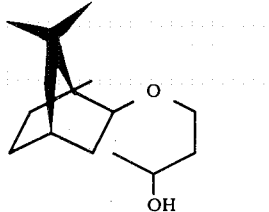<br>produced according to Example IV | An incense aroma with cedarwood undertones. | A walnut-like flavor. | A woody incense oriental and patchouli aroma and taste profile both prior to and on smoking in the main-stream and the side-stream. |
| 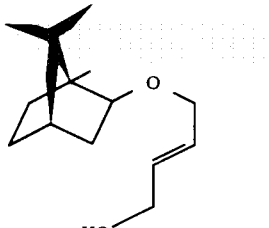<br>prepared according to Example VII | An onion, garlic and lavendar aroma profile with oniony animalic and sweaty undertones. | An onion garlic aroma and taste profile. | |
| 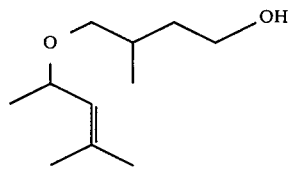<br>prepared according to Example IX | A camphoraceous, woody lavendar and spicy and floral aroma with patchouli and rosy undertones. | A walnut-like flavor. | |

TABLE II

| Ether Aldehyde | Perfumery Evaluation | Food Flavor Evaluation | Tobacco Flavor Evaluation |
|---|---|---|---|
| 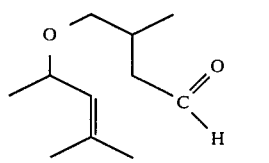<br>prepared according to Example VIII | A herbaceous, strong green leafy, pepper and spicy aroma profile with herbaceous peppery olibanum and diffusive amber undertones. | A floral flavor profile. | |

TABLE II-continued

| Ether Aldehyde | Perfumery Evaluation | Food Flavor Evaluation | Tobacco Flavor Evaluation |
|---|---|---|---|
| 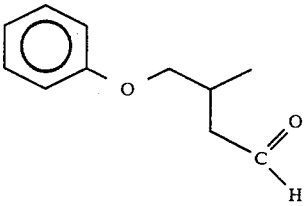<br>prepared according to Example X | A herbaceous sweet fruity chamomile-like aroma with caramellic undertones. | A fruity flavor. | A fruity aroma and taste profile both prior to and on smoking in the mainstream and the sidestream. |

When one or more of the ether carboxaldehydes and/or ether carbinols and reaction products containing some of our invention is used as a food flavor adjuvant, the nature of the co-ingredients included with said one or more ether carboxaldehydes and/or ether carbinols in formulating the product composition will also serve to alter the organoleptic characteristics of the ultimate foodstuffs treated therewith. As used herein, in regard to flavors, the term "alter" in its various forms means "supplying or imparting flavor character or notes to otherwise bland relatively tasteless substance or augmenting the existing flavor characteristic where a natural flavor is deficient in some regard or supplementing the existing flavor impression to modify its quality, character or taste".

As used herein, the term "foodstuff" includes both solid and liquid ingestible materials which usually do, but need not have nutritional value. Thus, foodstuffs include soups, convenience foods, beverages, dairy products, candies, fruits, cerals, soft drinks, snacks and the like.

Substances suitable for use herein as co-ingredients or flavoring adjuvants are well known in the art for such use being extensively described in the relevant literature. Apart from the requirement that any such material be "ingestibly" acceptable and thus non-toxic or otherwise non-deleterious, nothing particularly critical resides in selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2 and 3 tertiary butyl-4-hydroxyanisole), butylated hydroxy toluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agaragar; carrageenan; cellulose and cellulose derivatives such as carboxymethyl cellulose and methyl cellulose; natural and synthetic gums such as gum arabic, gum tragacanth; gelatine; proteinaceous materials; lipids; carbohydrates; starches pectins, and emulsifiers, e.g., mono- and diglycerides of fatty acids, skim milk powder, hexoses, pentoses, disaccharides, e.g., sucrose, corn syrup solids and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate hydrogenated tallow alcohol and the like.

Conditioners includes compounds such as bleaching and maturing agents, e.g., benzoyl peroxide, calcium peroxide, hydrogen peroxide and the like; starch modifiers such as peracetic acid, sodium chlorite; sodium hypochlorite, propylene oxide, succinic anhydride and the like, buffers and neutralizing agents, e.g., sodium acetate, ammonium bicarbonate, ammonium phosphate, citric acid, lactic acid, vinegar and the like, colorants, e.g., carminic acid, cochineal, tumeric and curcumin and the like; firming agents such as aluminum sodium sulfate, calcium chloride and calcium gluconate; texturizers; anti-caking agents, e.g., aluminum calcium sulfate and tribasic calcium phosphate; enzymes, yeast foods, e.g., calcium lactate and calcium sulfate; nutrient supplements, e.g., iron salts such as ferric phosphate, ferrous gluconate and the like, riboflavin, vitamins, zinc sources such as zinc chlorides, zinc sulfate and the like.

Other flavorants and flavor intensifiers include organic acids, e.g., acetic acid, butyric acid, caproic acid, caprylic acid, formic acid, 2-hexenoic acid, 3-hexenoic acid, isobutyric acid, isovaleric acid, propionic acid and valeric acid; ketones and aldehydes, e.g., acetaldehyde, acetone, acetyl methyl carbinol, acrolein, diacetyl, $\beta$,$\beta$-dimethylacrolein, hexanal, 2-hexenal, cis-3-hexenal, 4(p-hydroxyphenyl)-2-butanone, $\alpha$-ionone, $\beta$-ionone, and 2-pentenal; alcohols, such as 1-butanol, trans-2-buten-1-ol, ethanol, gernaiol, 1-hexanol, cis-3-hexen-1-ol, 3-methyl-3-buten-1-ol, 1-pentalol, 1-penten-3-ol; esters, such as butyl acetate, ethyl acetate, ethyl butyrate, ethyl crotonate, ethyl propionate, 2-hexenyl acetate, 2-hexenyl butyrate, hexyl acetate, hexyl butyrate, isoamyl acetate, isopropyl butyrate, methyl butyrate, methyl caproate, methyl caprylate, propyl acetate, amyl acetate, amyl butyrate, benzyl salicylate, dimethyl anthranilate, ethyl methylphenylglycidate, ethyl succinate, isobutyl cinnamate, and terpenyl acetate; essential oils such as jasmine absolute, rose absolute, orris absolute, lemon essential oil and vanilla; lactones; sulfides, e.g., methyl sulfide and other materials such as maltol and citral as well as natural orange oil, natural peppermint oil, strawberry juice concentrate and the like.

The specific flavoring adjuvants selected for use may be either solid or liquid, depending upon the desired physical form of the ultimate product, i.e., foodstuff, whether simulated or natural and should, in any event, be capable of providing an environment in which the one or more ether carboxaldehydes and/or ether carbinols of our invention can be dispersed or admixed to provide a homogeneous medium. In addition, the selection of one or more adjuvants as well as the quanities thereof, will depend upon the precise organoleptic natural orange character, natural orange juice character, natural peppermint character or natural walnut character desired in the finished product. Thus, in the case of flavoring compositions, ingredients selection will vary in accordance with the foodstuffs to which the flavor and aroma are to be imparted. In contradistinction, in the preparation of solid products, e.g., simulated foodstuffs, ingredients capable of providing normally solid compositions should be selected, such as various cellulose derivatives.

As will be appreceiated by those skilled in the art, the amount of one or more ether carboxaldehydes and/or ether carbinols of our invention employed in a particular instance can vary over a relatively wide range whereby its desired organoleptic effects (having reference to the nature of the product) are achieved. All parts and percentages given herein are by weight unless otherwise specified. Thus, correspondingly greater amounts would be necessary in those instances wherein the ultimate food composition to be flavored is relatively bland to the taste, whereas relatively minor quantities may suffice for the purposes of enhancing the composition merely deficient in natural flavor or aroma. Thus, the primary requirement is that amount which is effective, i.e., sufficient to alter the organoleptic characteristics of the parent composition, whether foodstuff, per se, or flavoring composition. Thus, the use of insufficient quantities of one or more ether carboxaldehydes and/or ether carbinols of our invention will, of course, substantially vitiate any possibility of obtaining the desired results while excess quantities prove needlessly cost and in extreme cases, may disrupt the flavor/aroma balance, thus proving self-defeating. Accordingly, the terminology "effect amount" and "sufficient amount" is to be accorded a significance in the context of the present invention consistent with the obtention of desired flavoring effects.

Thus, and with respect to ultimate food compositions, it has been found that quantities of one or more ether carboxaldehydes and/or ether carbinols of our invention ranging from a small but effective amount, e.g., 0.02 parts per million up to about 100 parts per million by weight based on total composition are suitable. Concentrations in excess of the maximum quantity stated are not normally recommended since they fail to provide commensurate enhancement of organoleptic properties. In those cases wherein the one or more ether carboxaldehydes and/or ether carbinols of our invention is added to the foodstuff as an integral component of the flavoring composition, it is, of course, essential that the total quantity of flavoring composition employed be sufficient to yield an effective ether carboxaldehyde and/or ether carbinol concentration in the foodstuff product.

The compositions described herein can be prepared according to conventional techniques well known as typified by cake batters and fruit juices and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by admixing one or more ether carboxaldehydes and/or ether carbinols of our invention with, for example, gum arabic, gum tragacanth, guar gum and the like and thereafter spray-drying the resultant mixture whereby to obtain the particulate solid product. Prepared flavor mixes in powder form, e.g., an orange-flavored powder or a peppermint-flavored powder are obtained by mixing dry solid components, e.g., starch, sugar and the like and one or more ether carboxaldehydes and/or ether carbinols in a dry blender until the requisite degree of uniformity is achieved.

It is presently preferred to combine one or more of the ether carboxaldehydes and/or ether carbinols of our invention with the following adjuvants:

Parahydroxybenzyl acetone;
Vanillin;
Maltol;
$\beta$-Ionone;
$\beta$-Ionone;
Isobutyl acetate;
Ethyl butyrate;
Dimethyl sulfide;
Acetic acid;
Acetaldehyde;
4-(2,6,6-trimethyl-1,3-cyclohexadien-1-yl)-2-butanone;
4-(6,6-dimethyl-2-methylene-3-cyclohexen-1-yl)-2-butanone;
2-(4-hydroxy-4-methylpentyl)norbornadiene produced according to Example I of U.S. Pat. No. 3,911,028;
$\beta$-Damascone(1-crotonyl-2,6,6-trimethylcyclohex-1-ene);
$\beta$-Damascenone(1-crotonyl-2,6,6-trimethylcyclohexa-1,3-diene);
Beta-cyclohomocitral(2,6,6-trimethylcyclohex-1-ene carboxaldehyde)
Isoamyl butyrate;
Cis-3-hexenol-1;
Elemecine(4-allyl-1,2,6-trimethoxybenzene);
Isoelemecine(4-propenyl-1,2,6-trimethoxybenzene);
Cis-2-3-methyl pentenoic acid;
Ethyl-2-methyl-3-pentenoate;
Isobutyl-cis-2-methyl-3-pentenoate;
2-Ethylidene-3-pentenal;
Orange oil;
Lemon oil;
Peppermint oil;
Strawberry juice extract;
Raspberry juice extract;
Cranberry juice extract;
Mango extract;
Pickled mango extract; and
Pulverized walnuts.

One or more ether carboxaldehyde derivatives and/or ether carbinol derivatives prepared in accordance with the processes of our invention and one or more auxiliary perfume ingredients, including, for example, alcohols other than those of our invention; aldehydes other than those of our invention; ketones; topenic hydrocarbons; nitriles; esters; lactones; natural essential oils; and synthetic essential oils may be admixed so that the combined odors of the individual components produce a pleasant and desired fragrance, particularly and preferably in the green, orange, ozoney, patchouli, incense, sandalwood, musk, cedarwood, minty, lavender, herbaceous, woody and chamomile fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the overall sensory effect of the perfume composition will be at least the sum total of the effects of each of the ingredients. Thus, one or more of the ether carboxaldehyde derivatives and/or ether carbinol derivatives prepared in accordance with the processes of our invention can be used to alter, modify or enhance the aroma characteristics of a perfume composition, for example, by utilizing or moderating the olfactory reaction contributed by another ingredient in the composition.

The amount of one or more ether carboxaldehyde derivatives and/or ether carbinol derivatives prepared in accordance with the processes of our invention which will be effective in perfume compositions as well as in perfumed articles (e.g., anionic, nonionic, cationic and zwitterionic solid or liquid detergents, soaps, fabric softener compositions, drier-added fabric softener articles, optical brightener compositions, perfumed polymers and textile sizing agents) and colognes depends on many factors, including the other ingredients, their amounts and the effects which are desired. It has been found that perfume compositions containing as little as 0.01% of one or more of the ether carboxaldehydes derivatives and/or ether carbinol derivatives of our invention prepared in accordance with the processes of our invention and less than 50% of one or more of the ether carboxaldehyde derivatives and/or ether carbinol derivatives prepared in accordance with the processes of our invention or even less (e.g., 0.005%) can be used to impart, augment or enhance ozoney, fresh air dried cloth-like, green, orange, nutty, woody, minty, patchouli-like, incense-like, oniony, garlic, lavender-like, herbaceous, leafy, pepper-like, spicy, camphoraceous, woody, fruity and chamomile-like aroma nuances with patchouli-like, cedarwood, oniony, animalic sweaty, herbaceous, peppery, olibanum, diffusive amber, rosey and caramellic undertones to soaps, cosmetics, solid or liquid anionic, nonionic, cationic and zwitterionic detergents, fabric softener compositions, fabric softener articles, optical brightener compositions, textile sizing compositions, perfumed polymers or other products. The amount employed can range up to 70% of the fragrance components and will depend on considerations, of course, nature of the end product, the effect desired on the finished product and the particular fragrance sought.

One or more ether carboxaldehyde derivatives and/or ether carbinol derivatives prepared in accordance with the processes of our invention are useful (taken alone or together with other ingredients in perfume compositions) as (an) olfactory component (s) in detergents and soaps, space odorants and deodorants, perfumes, colognes, toilet water, bath preparations, such as creams, deodorants, hand lotions and sun screens; powders, such as, talcs, dusting powders, face powders, and perfumed polymers and articles of manufacture produced from said perfumed polymers, e.g., garbage bags, children's toys and the like. When used as (an) olfactory component (s) as little as 0.2% of one or more of the ether carboxaldehyde derivatives and/or ether carbinol derivatives prepared in accordance with the processes of our invention will suffice to impart, augment or enhance intense ozoney, fresh air dried cloth-like, green, orange, nutty, woody, minty, patchouli-like, incense-like, oniony, garlic-like, lavender-like, herbaceous, leafy, pepper, spice, camphoraceous, woody, sweety fruit and chamolime-like aroma nuances with patchouli-like, cedarwood-like, oniony, animalic sweaty, herbaceous, peppery olibanum, diffusive amber, rosey and caramellic undertones to floral, piney, lavender, spicy and patchouli formulations. Genernally, no more than 6% of one or more of the ether carboxaldehyde derivatives and/or ether carbinol derivatives of our invention based on the ultimate end product as required in the perfumed article composition. Accordingly, the range of ether carboxaldehydes and/or ether carbinols in the perfumed article is from about 0.2% by weight of the ether carboxaldehyde and/or ether carbinol up to about 6% by weight of the ether carboxaldehyde and/or ether carbinol based on the total weight of the perfumed article.

In addition, the perfumed composition or fragrance composition of our invention can contain a vehicle or carrier for one or more of the ether carboxaldehyde derivatives and/or ether carbinol derivatives prepared in accordance with the processes of our invention. The vehicle can be a liquid, such as, a non-toxic alcohol, e.g., ethyl alcohol, a non-toxic glycol, e.g., propylene glycol or the like. The carrier can also be an absorbant solid, such as, gum (e.g., gum arabic or gum orzentane) or components for incapsulating the composition (such as, gelatin as by coacervation) or such as, urea formaldehyde polymer forming a capsule shell around a liquid perfumed center.

Our Invention also relates to the utilization of controlled released technology for the controlled release or perfumes into gaseous environments from polymers such as mixtures of epsilon polycaprolactone polymers and polyethylene which polyepsilon caprolactone polymers are defined according to at least one of the structures:

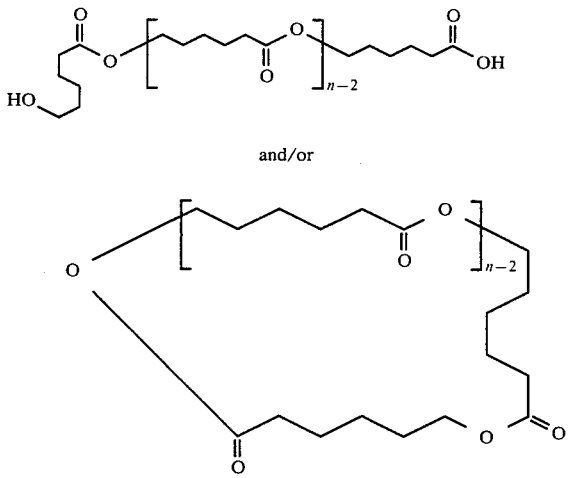

and/or wherein "n" is from about 50 up to about 1,200 with the proviso that the average "n" in the system varies from about 150 up to about 700 according to the mathematical statement:

$[700 \geq \bar{n} \geq 150]$ with the term $\bar{n}$
being the average number of repeating monomeric units for the epsilon polycaprolactone polymer. The perfumed material's release rate from such polymer mixture is close to "zero order". As a general rule, the release rate in a polymeric matrix is proportional to $t^{-\frac{1}{2}}$ until about 60% of the functional fluid is released from the polymeric matrix. The release rate thereafter is related exponentially to time as a general rule according to the equation:

$$dM_t/dt = k_1 e^{-k_2 t}$$

wherein $k_1$ and $k_2$ are constants. According to Kydonieus, "Controlled Release Technologies: Methods, Theory, and Applications" (cited, supra) the amount of perfume composition released is proportional to time as long as the concentration of perfume material present, e.g., the ether carboxaldehydes and/or ether carbinols of our invention is higher than the solubility of the agent in the matrix. Thus, such dispersed systems are similar to the dissolved systems except that instead of a decreased release rate after 60% of the perfume material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release being constant (zero order) as long as the surface area does not change during the erosion process. This is the case with the polymers containing the ether carboxaldehydes and/or ether carbinols of our invention.

The polyepsilon caprolactone polymers useful in practicing our invention are more specifically described in the brochure of the Union Carbide Corporation, 270 Park Avenue, New York, N.Y. 10017, entitled NEW POLYCAPROLACTONE THERMOPLASTIC POLYMERS PCL-300 AND PCL-700. These polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating monomeric units is about 300. Regarding PCL-700, the average number of repeating monomeric units is 700.

The polyepsilon caprolactone homopolymers which are ultimately taken in admixture with such materials as polyethylene useful in the practice of our invention may also be stabilized using stabilizers as defined in U.S. Pat. No. 4,360,682 issued on Nov. 23, 1982, the specification for which is incorporated herein by reference. The stabilizing materials which stabilize the polyepsilon caprolactone useful in conjunction with our invention against discoloration are dihydroxybenzenes such hydroquinone or compounds having the formula:

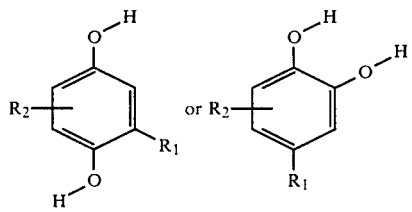

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfere with the functional fluids dissolved and/or absorbed into the polymeric matrix.

The method of incorporating the ether carboxaldehydes and/or ether carbinols of our invention or perfume compositions containing same into the polymers may be according to the techniques of U.S. Pat. No. 3,505,432 issued on Apr. 7, 1970 (the specification for which is incorporated by reference herein) or U.S. Pat. No. 4,247,498 issued on Jan. 27, 1981, the disclosure of which is incorporated by reference herein.

Thus, for example, a first amount of liquid polyethylenepolyepsilon caprolactone polymer mixture (50:50) is mixed with one of the ether carboxaldehydes and/or ether carbinols of our invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained, is solidified subsequent to or prior to ultimate casting into a utilitarian shape.

Thus, in accordance with one aspect of our invention, the imparting of scent is effected in two stages. In a first stage, a 50:50 (weight:weight) polyepsilon caprolactone, e.g., PCL-700: polyethylene in molten form is admixed with a high percentage of one of the ether carboxaldehydes and/or ether carbinols of our invention and the mixture is solidified in the form of pellets or beads. These pellets or beads thus contain a high percentage of ether carboxaldehydes and/or ether carbinols (e.g., up to 45% by weight of the entire mixture) and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification 1,589,201 published on May 7, 1981, the specification for which is incorporated by reference herein.

In accordance with the present invention at least one of the ether carboxaldehydes and/or ether carbinols of our invention is added to the polymer in a large closed container or drum which is maintained under controlled temperature conditions while the polymer in a melted condition is mixed with at least one of the ether carboxaldehydes and/or ether carbinols under agitation.

In order that the perfume be added uniformly to the polymer, the temperature of the melt is constantly controlled during the process. The polymer-perfume mixture is then directed through an elongated conduit or pipe element having a plurality of orifices adjacent to the lower most portion thereof. The polymer enriched by at least one of the ether carboxaldehydes and/or ether carbinols of our invention is permitted to drip through the orifices onto a continuously moving, cooled conveyor upon which the polymer containing at least one of the ether carboxaldehydes and/or ether carbinols of our invention solidifies into small size pellets with the perfume imprisoned therein. The apparatus useful in conjuction with this process, advantageously includes a conveyor of a material which will not adhere to the polymer which contains at least one of the ether carboxaldehydes and/or ether carbinols of our invention.

In order that the droplets form into uniform pellets or beads, the conveyor is continuously washed with a liquid, such as water to maintain the surface relatively cool. The pellets are delivered by the conveyor into a container and packaged for shipment.

Furthermore, one or more of the ether carboxaldehydes and/or ether carbinols of our invention prepared in accordance with the processes of our invention are capable of supplying and/or potentiating certain flavor and aroma notes usually lacking in many smoking tobacco flavors and substitute tobacco flavors heretofore provided.

As used herein in regard to smoking tobacco flavors, the terms "alter" and "modify", in their various forms, mean "supplying or imparting flavor character or note to otherwise bland smoking tobacco, smoking tobacco substitutes, or smoking tobacco flavor formulations or augmenting the existing flavor characteristic where a natural flavor is deficient in some regard or supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of smoking tobacco or a smoking tobacco substitute or a smoking tobacco flavor.

Our invention thus provides an organoleptically improved smoking tobacco product and additives therefor, as well as methods of making the same which overcome specific problems heretofore encountered in which specific desired woody, green, herbaceous and spicy aroma and taste nuances prior to and on smoking in both the main stream and in the side stream are created or enhanced and may be readily controlled and maintained at the desired uniform level regardless of variations in the tobacco components of the blend.

This invention further provides various improved smoking tobacco additives and methods, whereby, various woody, incense-like, oriental and patchouli nuances are imparted (on smoking in the main stream and in the side stream) to smoking tobacco products and may be readily varied and controlled to produce the desired uniformed flavor characteristics, particularly, insofar as "oriental" like tobacco characteristics are concerned.

In carrying out this aspect of our invention, we add to smoking tobacco materials or a suitable substitute therefor (e.g., dried lettuce leaves) an aroma and flavor additive containing as an active ingredient at least one or more of the ether carboxaldehydes and/or ether carbinols prepared in accordance with the processes of our invention.

In addition to one or more of the ether carboxaldehydes and/or ether carbinols prepared in accordance with the processes of our invention, other flavoring and aroma additives may be added to the smoking tobacco materials or substitute therefor either separately or in admixture with one or more of the ether carboxaldehydes and/or ether carbinols of our invention as follows:

(i) Synthetic Materials

Beta-ethyl-cinnamaldehyde;
Beta-cyclohomocitral;
Eugenol;
Dipentene;
β-Damascenone;
β-Damascone;
Maltol;
Ethyl maltol;
Delta-undecalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethylnaphtho[2,1b]furan;
4-Hydroxy hexanoic acid, gamma lactone; and
Polyisoprenoid hydrocarbons defined in Example V of U.S. Pat. No. 3,589,372 issued on June 29, 1971.

(ii) Natural Oils

Celery seed oil;
Coffee extract;
Bergamot oil;
Cocoa extract;
Nutmeg oil; and
Origanum oil.

An aroma and flavoring concentrate containing one or more of the ether carboxaldehydes and/or ether carbinols prepared in accordance with the process of our invention, and, if desired, one or more of the above-identified additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixture thereof. The proportions of flavoring additives may be varied in accordance with taste but insofar as enhancement or the imparting of natural and/or spicy notes, we have found that satisfactory results are obtained if the porportion by weight of the sum total of one or more of the ether carboxaldehydes and/or ether carbinols is between 250 ppm and 1,500 ppm (0.025%–0.15%) of the active ingredients to the smoking tobacco material. We have further found that satisfactory results are obtained if the proportion by weight of the sum total of one or more of the ether carboxaldehydes and/or ether carbinols of our invention is between 2,500 and 15,000 ppm (0.25%–1.50%).

Any convenient method for incorporation of one or more of the ether carboxaldehydes and/or ether carbinols prepared in accordance with the processes of our invention in the tobacco product may be employed. Thus, one or more of the ether carboxaldehydes and/or ether carbinols of our invention taken alone or along with other flavoring additives may be dissolved in a suitable solvent, such as ethanol, pentane, diethyl ether and/or other volatile organic solvents and the resulting solution may either be sprayed on the cured, cased and blended tobacco material or the tobacco material may be dipped into such solution. Under certain circumstances, a solution containing one or more of the ether carboxaldehydes and/or ether carbinols of our invention taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the smoking tobacco or substitute therefor need be treated and the thus treated tobacco may be blended with other tobaccos before the ultimate tobacco product is formed. In such cases, the tobacco treated may have one or more of the ether carboxaldehydes and/or ether carbinols of our invention in excess of the amounts or concentrations above-indicated so that when blended with other tobaccos, the final product will have the percentage within the indicated range.

In accordance with one specific example of our invention, an aged, cured and shredded domestic Burley tobacco is sprayed with a 20% ethyl alcohol solution of a 50:35:15 weight:weight:weight mixture of compounds containing materials having the following structures (in the order stated):

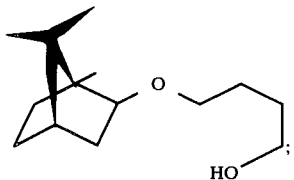

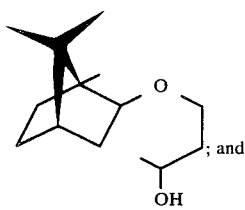
; and

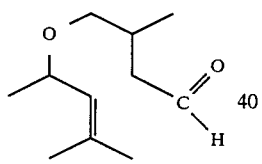

respectively in an amount to provide the tobacco composition containing 800 ppm by weight of the above-mentioned ether carboxaldehydes and/or ether carbinols on a dry basis.

Thereafter, the alcohol is removed by evaporation and the tobacco is manufactured into cigarettes by the usual techniques. The cigarettes, when treated as indicated, have a desired and pleasing aroma prior to smoking which can be described as woody, incense-like, oriental, minty and patchouli-like and, on smoking, in the main stream and in the side stream as spicy, oriental-like, turkish tobacco-like, and woody with a slight mouth coating effect.

While our invention is particularly useful in the manufacture of smoking tobacco, such as cigarette tobacco, cigar tobacco, and pipe tobacco, other smoking tobacco products formed from sheeted tobacco dust or fines may also be used. Likewise, one or more of the ether carboxaldehydes and/or ether carbinols of our invention can be incorporated with materials such as, filter tip materials, seam paste, packaging materials and the like which are used along with tobacco to form a product adapted for smoking. Furthermore, one or more of the ether carboxaldehydes and/or ether carbinols of our invention can be added to certain tobacco substitutes of natural or synthetic origin (e.g., dried lettuce leaves) and accordingly, by the term "tobacco" is used throughout this specification is meant any composition intended for human consumption by smoking or otherwise whether composed of tobacco plant parts or substitute materials or both.

The following Examples I-X serve to illustrate processes for preparing the ether carboxaldehydes and/or ether carbinols of our invention. The examples following Example X are illustrative of the organoleptic utilities of the ether carboxaldehydes and ether carbinols of our invention. All parts and percentages given herein are by weight unless otherwise specified.

EXAMPLE I

PREPARATION OF 4-(p-CUMENYLOXY)-3-METHYLBUTYRALDE-HYDE

Reaction:

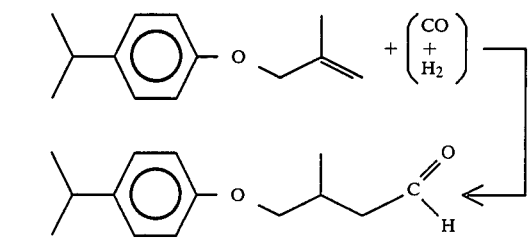

Into a 500 cc autoclave is placed:
200 grams of the compound having the structure:

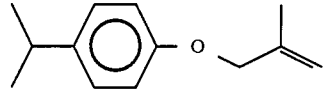

and 0.1 gram of Rhodium acetoacetate dicarbonyl.

The autoclave is sealed and pressurized to 1,000 psig at 120° using a 50:50 mole:mole mixture of carbon monoxide and hydrogen and maintained at that pressure and temperature for a period of 14.5 hours. GLC analysis indicates 83% product formed.

The reaction mass is cooled and the autoclave is opened. The contents are filtered and the liquid material is distilled on a 2" splash column yielding the following fractions:

| Fraction No. | Vapor Temp. (°C.) | Liquid Temp. (°C.) | Vacuum mm/Hg. Pressure | Weight of Fractions (gms) |
|---|---|---|---|---|
| 1 | 97/103 | 133/140 | 3.5 | 18.3 |
| 2 | 104 | 140 | 3.0 | 27.8 |
| 3 | 134 | 158 | 2.4 | 47.1 |
| 4 | 140 | 180 | 4.0 | 39.5 |

Fractions 2, 3 and 4 are bulked and redistilled on a micro Vigreux column yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 65/ | 142/ | 3.4 | 2.9 |
| 2 | 75 | 145 | 3.4 | 3.2 |
| 3 | 73 | 148 | 3.4 | 3.0 |
| 4 | 70 | 150 | 3.4 | 2.3 |
| 5 | 98 | 155 | 3.4 | 7.6 |
| 6 | 95 | 157 | 3.4 | 7.6 |
| 7 | 80 | 164 | 3.6 | 11.5 |
| 8 | 94 | 172 | 3.6 | 1.5 |
| 9 | 104 | 193 | 3.6 | 3.1 |
| 10 | 100 | 200 | 3.6 | 5.7 |
| 11 | 80 | 220 | 3.6 | 3.2 |

FIG. 1 is the GLC profile for Fraction 4 of the foregoing distillation.

The peak indicated by reference numeral "10" is the peak for the compound having the structure:

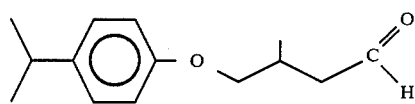

FIG. 2 is the NMR spectrum for the peak indicated by reference numeral "10" on FIG. 1 for the compound having the structure:

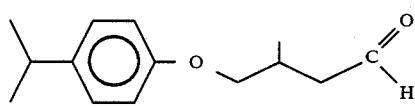

(Conditions: CFCl₃ solvent; Field strength: 100 MHz).

EXAMPLE II

PREPARATION OF 4(p-CUMENYLOXY)-3-METHYL-1-BUTANOL

Reaction:

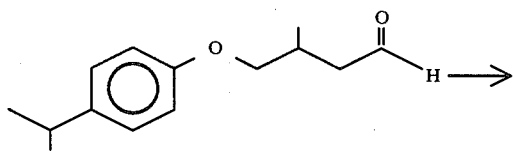

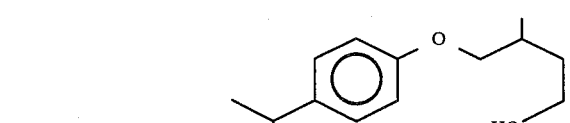

Into a one liter reaction flask is placed 56.7 grams (1.5 moles) of sodium borohydride and 200 ml of anhydrous isopropyl alcohol. Over a period of 45 minutes, 225 grams of the aldehyde having the structure:

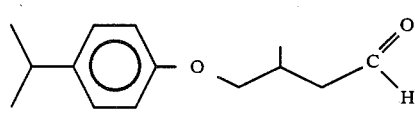

is added to the reaction mass. The reaction mass is maintained at 20° C. for a period of three hours with stirring.

At the end of the three hour period, the reaction mass is filtered and the filtrate is washed with water until neutral. The crude reaction mass is then distilled through a 2" splash column followed by a fractional distillation through a micro Vigreux column. The distillation through the micro Vigreux column yields the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 65 | 142 | 3.4 | 2.9 |
| 2 | 75 | 145 | 3.4 | 3.2 |
| 3 | 73 | 148 | 3.4 | 3.0 |
| 4 | 70 | 150 | 3.4 | 2.3 |
| 5 | 98 | 155 | 3.4 | 7.6 |
| 6 | 95 | 157 | 3.4 | 7.6 |
| 7 | 80 | 164 | 3.6 | 11.5 |
| 8 | 94 | 172 | 3.6 | 1.5 |
| 9 | 104 | 193 | 3.6 | 3.1 |
| 10 | 100 | 200 | 3.6 | 5.7 |
| 11 | 80 | 220 | 3.6 | 3.2 |

FIG. 3A is the GLC profile for the crude reaction product containing the compound having the structure:

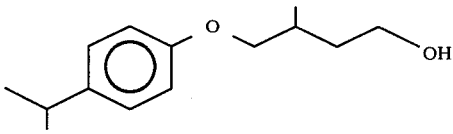

FIG. 3B is the GLC profile for fraction 5 of the foregoing distillation containing the compound having the structure:

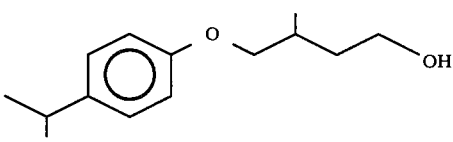

FIG. 4 is the NMR spectrum for the peak indicated by reference "50" of the GLC profile of FIG. 3B for the compound having the structure:

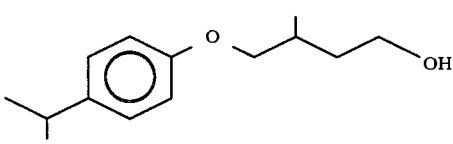

(Conditions: Field strength: 100 MHz; solvent: CFCl₃).

EXAMPLE III

PREPARATION OF 4-(2-BORNYLOXY) BUTYRALDEHYDE

Reaction:

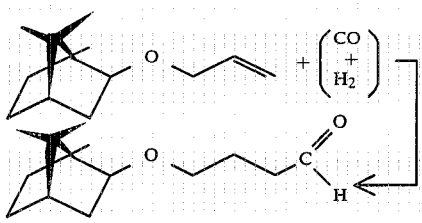

Into a 500 ml autoclave are placed the following ingredients:

Isobornyl allyl ether having the structure:

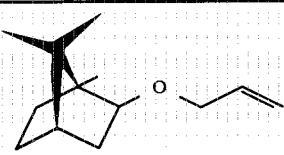

194 grams (1 mole)

| | |
|---|---|
| Triphenylphosphine | 2.0 grams |
| Rhodium Chloride-mono-carbonyl-triphenylphosphine | 0.2 grams |
| Toluene | 50.0 ml |

The autoclave is sealed and pressurized to 500 psig using a 50:50 mole:mole mixture of carbon monoxide and hydrogen. The autoclave is heated to 200° and maintained at 500–700 psig for a period of 13 hours. At the end of the 13 hour period, the autoclave is cooled and opened yielding 462.9 grams of product (including toluene).

The reaction product is then distilled through a 12" Goodloe column yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 119/ | 165/ | 4.0 | 13.9 |
| 2 | 125 | 175 | 3.0 | 16.1 |
| 3 | 156 | 244 | 3.0 | 17.7 |
| 4 | 195 | 284 | 3.0 | 13.0 |

Fractions 2, 3 and 4 are bulked and redistilled through a spinning band column yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | /94 | /134 | 2.8 | 9.7 |
| 2 | 95 | 140 | 2.6 | 8.7 |
| 3 | 62 | 147 | 2.6 | 3.5 |
| 4 | 102 | 163 | 2.4 | 2.8 |
| 5 | 114 | 178 | 2.4 | 3.3 |
| 6 | 70 | 194 | 2.8 | 5.9 |
| 7 | 64 | 240 | 2.9 | 4.4 |

The resulting product contains 70 percent by weight of the compound having the structure:

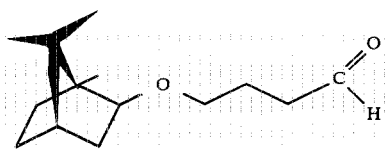

and 30 percent by weight of the compound having the structure:

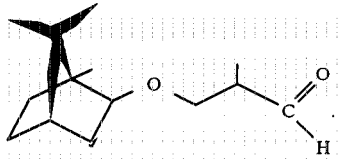

FIG. 5 is the GLC profile of bulked fractions 2–4 of the first distillation. This material contains a mixture of compounds having the structures:

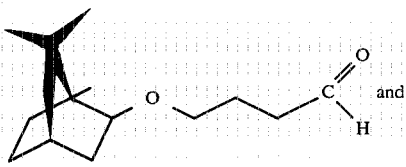 and

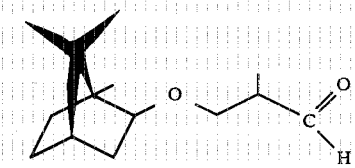

FIG. 6 is the GLC profile for fraction 5 of the spinning and distillation and contains the compounds having the structures:

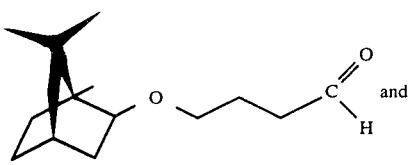 and

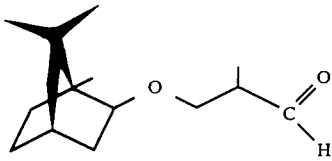

FIG. 7 is the NMR spectrum for the mixture of compounds containing 70 percent by weight of the compound having the structure:

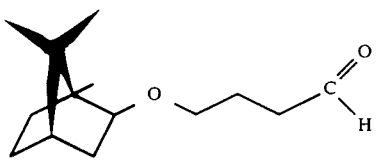

and 30 percent by weight of the compound having the structure:

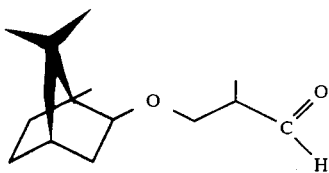

(Conditions: CFCl₃ solvent; 100 MHz field strength).

EXAMPLE IV

PREPARATION OF 4-(2-BORNYLOXY)-1-BUTANOL)

Reaction:

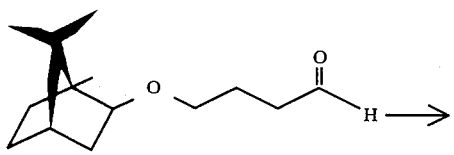

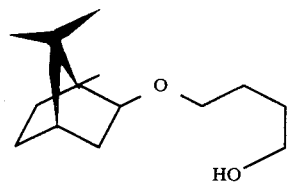

Into an one liter reaction flask equipped with stirrer, thermometer, reflux condenser and heating mantel is placed 200 ml of anhydrous isoproply alcohol and 56.7 grams (1.5 moles) of sodium borohydride. The resulting mixture is heated to reflux and during refluxing, over a 45 minute period, the aldehyde having the structure:

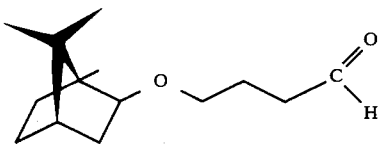

produced according to Example III is added to the reaction mass. The reaction mass is then continued to be stirred at reflux for a period of three hours. At the end of the three hour period, the reaction mass is cooled to room temperature and the undissolved sodium borohydride is filtered. The reaction mass is then washed with water until neutral. The crude reaction mass, weighing 309.3 grams, is then rushed over through a 2" splash column yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 95/ | 119/ | 1.3 | 2.2 |
| 2 | 100 | 120 | 1.4 | 9.4 |
| 3 | 104 | 130 | 1.4 | 30.8 |
| 4 | 105 | 135 | 1.5 | 34.4 |
| 5 | 107 | 145 | 1.6 | 37.0 |
| 6 | 106 | 173 | 1.7 | 16.3 |
| 7 | 106 | 179 | 1.7 | 1.0 |

FIG. 8 is GLC profile for the crude reaction product containing the compounds having the structure:

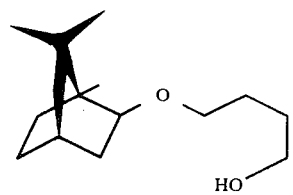

and

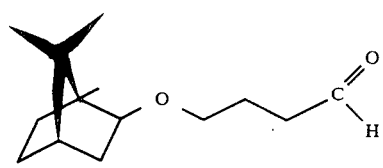

FIG. 9 is the GLC profile for fraction 2 of the foregoing distillation product containing the compound having the structure:

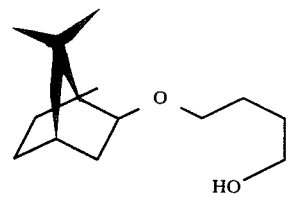

FIG. 10 is the NMR spectrum for the compound having the structure:

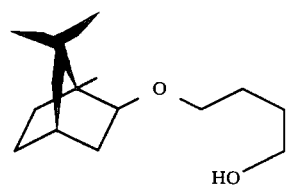

produced according to this Example (Conditions: Field strength: 100 MHz; solvent: CFCl₃).

FIG. 11 is the infrared spectrum for the compound having the structure:

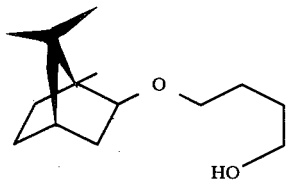

produced according to this Example.

EXAMPLE V

PRODUCTION OF 4-(2-BORNYLOXY)-1-BUTANOL

Reaction:

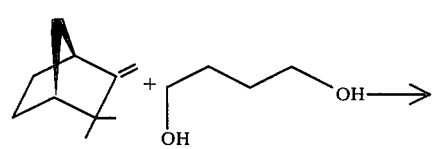

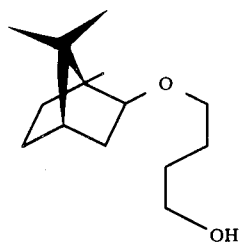

Into an one liter reaction flask equipped with stirrer, thermometer and reflux condenser is placed 500 grams of 1,4-butanediol and 15 grams of born trifluoride. The reaction mass is heated to 80° C. Over a period of one hour, a mixture of 500 grams of camphene and 500 grams of 1,4-butanediol is added to the reaction mass. During the addition period, the reaction mass is maintained at 79°-80° C. with stirring. The reaction mass is continued to be stired at 80° C. for a period of seven hours. At the end of the seven hour period, the reaction mass is washed with water and extracted with toluene. The organic phase is then separated and is washed with saturated sodium carbonate solution. The thus washed material is then dried over anhydrous sodium sulfate and distilled on a 12" Goodloe column yielding the following fractions.

| Fraction No. | Vapor Temp. (°C.) | Liquid Temp. (°C.) | Vacuum mm/Hg. Pressure | Weight of Fraction (gms) |
|---|---|---|---|---|
| 1 | 118/127 | 157/143 | 1.2/3 | 39 |
| 2 | 128 | 143 | 2.7 | 38 |
| 3 | 128 | 143 | 2.8 | 42 |
| 4 | 128 | 143 | 2.7 | 46 |
| 5 | 128 | 143 | 2.8 | 35 |
| 6 | 128 | 145 | 2.8 | 55 |
| 7 | 129 | 150 | 2.8 | 39 |
| 8 | 133 | 207 | 3.0 | 27 |

FIG. 12 is the GLC profile for crude reaction product for this Example containing the compound having the structure:

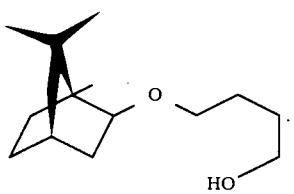

FIG. 13 is the NMR spectrum for fraction 4 of the foregoing distillation product containing the compound having the structure:

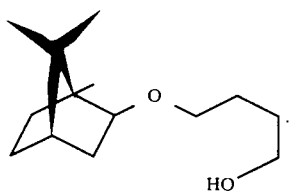

EXAMPLE VI

PREPARATION OF 4-(2-BORNYLOXY)2-BUTANOL

Reaction:

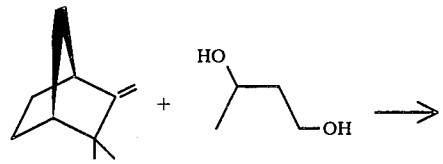

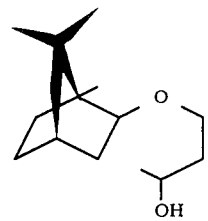

Into a one liter reaction vessel equipped with a stirrer, thermometer, reflux condenser and heating mantel is placed 340 grams of t,3-butanidiol and 10 grams of bron trifluoride. The reaction mass is heated to 80° C. and while maintaining the reaction mass at 80° C., 340 grams of camphene is added over a two hour period. At the end of the camphene feeding period, the reaction mass is stirred at a temperature of 80° C. for a period of 18 hours.

After the 18 hour period, the reaction mass is quenched with water and the reaction mass is washed with saturated sodium carbonate solution until neutral. The aqueous phase is separated from the organic phase. The aqueous phase is extracted with toluene and the toluene extracts are added to the organic phase. The resulting organic material is then charged to an evaporator and the toluene solvent is recovered.

The resulting product is distilled on a column packed with splash saddles yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 93/ | 127/ | 5.0 | 7.0 |
| 2 | 115 | 127 | 5.0 | 15.0 |
| 3 | 123 | 136 | 4.8 | 211.0 |
| 4 | 175 | 220 | 3.8 | 190.0 |

FIG. 14 is the GLC profile for the crude reaction product containing the compound having the structure:

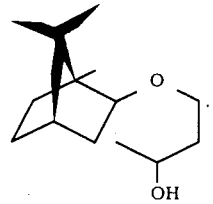

FIG. 15 is the NMR spectrum for fraction 2 of the foregoing distillation product containing the structure:

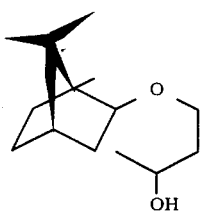

(Conditions: Field strength: 100 MHz; solvent: CFCl₃).

EXAMPLE VII

PREPARATION OF 4-(2-BORNYLOXY)-2-BUTEN-1-OL

Reaction:

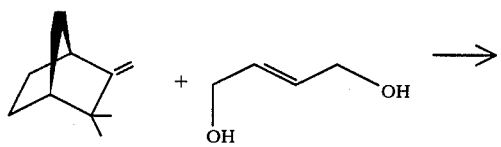

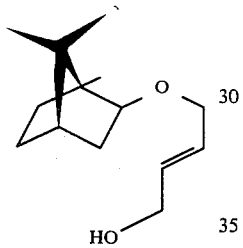

Into a two liter reaction vessel equipped with stirrer, thermometer, heating mantel and reflux condenser is placed 1000 grams (7.35 moles) of 2-pentene-1,4-diol and 15 grams of boron trifluoride etherate. The reaction mass is then heated to 80° C. Over a period of two hours while maintaining the reaction mass at 80° C., 500 grams (3.7 moles) of camphene is added. The reaction is continued to be stirred at 80° C. for a period of 12.5 hours after the feeding of the camphene.

At the end of the 12.5 hour period, the reaction mass is cooled to room temperature, quenc-ed with water and neutralized with saturated sodium carbonate. The organic phase is then distilled on a 2" splash column packed with saddles yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 80/102 | 118/124 | 1.2 | 14.0 |
| 2 | 110 | 126 | 1.2 | 19.0 |
| 3 | 120 | 131 | 1.2 | 64.0 |
| 4 | 130 | 143 | 1.2 | 205.0 |
| 5 | 155 | 180 | 1.2 | 142.0 |
| 6 | 170 | 220 | 1.2 | 60.0 |

Fractitons 2–5 are bulked and redistilled on a 12" Goodloe column yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 128/130 | 153/151 | 2.6 | 16.0 |
| 2 | 130 | 146 | 2.6 | 18.0 |
| 3 | 131 | 147 | 2.6 | 20.0 |
| 4 | 131 | 147 | 2.6 | 19.0 |
| 5 | 131 | 147 | 2.6 | 27.0 |
| 6 | 131 | 147 | 2.6 | 22.0 |
| 7 | 131 | 147 | 2.6 | 18.0 |
| 8 | 131 | 147 | 2.6 | 25.0 |
| 9 | 131 | 147 | 2.6 | 26.0 |
| 10 | 131 | 148 | 2.6 | 23.0 |
| 11 | 131 | 149 | 2.6 | 27.0 |
| 12 | 132 | 150 | 2.6 | 20.0 |
| 13 | 131/132 | 150/152 | 2.5 | 21.0 |
| 14 | 132 | 155 | 2.5 | 26.0 |
| 15 | 132 | 162 | 2.5 | 25.0 |
| 16 | 132 | 187 | 2.5 | 20.0 |
| 17 | 139 | 207 | 2.5 | 13.0 |
| 18 | 155 | 210 | 2.5 | 8.0 |

FIG. 16 is the GLC profile for the crude reaction product containing the compound having the structure:

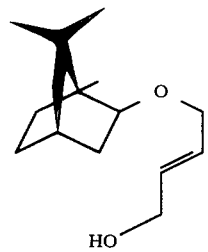

(Conditions: SE 30 column programmed at 100°–200° C. at 8° C. per minute).

FIG. 17 is the NMR spectrum for fraction 4 of the foregoing distillation product containing the compound having the structure:

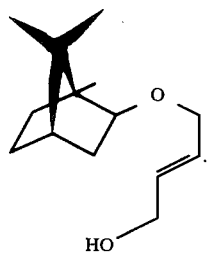

EXAMPLE VIII

PREPARATION OF 4-[1,3-DIMETHYL-2-BUTENYL)OXY]3-METHYL-BUTYRALDEHYDE

Reaction:

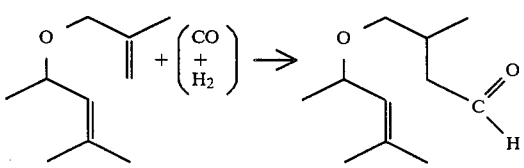

Into a high-pressure oxo-reactor is placed 98 grams of the methallyl ether having the structure:

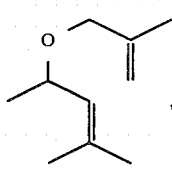

0.3 grams of rhodium-chlorocarbonyl (triphenyl phosphine), 3 grams of triphenyl phosphine and 300 ml of anhydrous toluene. The oxo-reactor is sealed, heated to 130° C. and pressurized to 1000 psig with a 50:50 mole:-mole mixture of carbon monoxide and hydrogen. The oxo-reactor is stirred for a period of one hour at 1000 psig and 130° C. and then the temperature is raised to 140° C. The oxo-reactor is then stirred for a period of four hours at 140° C. The reaction mass is then cooled to room temperature, and the reaction is opened. The reaction product is then filtered. The filtrate weighs 355.5 grams. The filtrate is then distilled on a 2″ splash column yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | /53 | /63 | 10.4 | 58.2 |
| 2 | 52 | 67 | 10.0 | 67.5 |
| 3 | 50 | 127 | 9.5 | 70.1 |
| 4 | 61 | 97 | 7.0 | 8.9 |
| 5 | 89 | 95 | 7.0 | 12.2 |
| 6 | 82 | 98 | 7.9 | 10.4 |
| 7 | 85 | 97 | 4.9 | 17.6 |
| 8 | 80 | 105 | 3.7 | 12.5 |
| 9 | 78 | 123 | 3.6 | 10.9 |
| 10 | 80 | 137 | 3.6 | 7.5 |
| 11 | 86 | 210 | 3.8 | 6.9 |

FIG. 18 is the GLC profile for fraction 4 of the foregoing distillation product containing the compound having the structure:

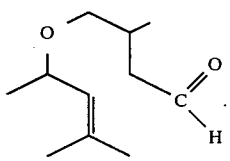

FIG. 19 is the NMR spectrum for fraction 8 of the foregoing distillation containing the compound having the structure:

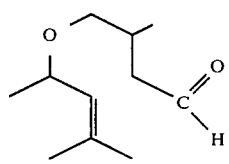

(Conditions: Field strength: 100 MHz; solvent: CFCl₃).

EXAMPLE IX

PREPARATION OF 4-[(1,3-DIMETHYL-2-BUTENYL)OXY]-3-METHYL-1-BUTANOL

Reaction:

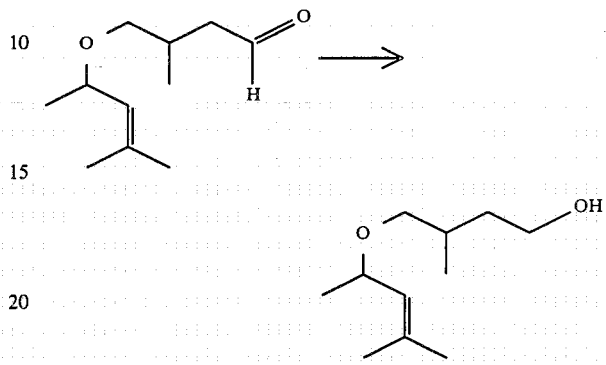

Into a 250 cc reaction vessel equipped with stirrer, thermometer, reflux condenser and heating mantel is placed 10 grams of sodium borohydride and 100 ml anhydrous isopropyl alcohol.

While maintaining the reaction mass at room temperature, 66.5 grams of the aldehyde produced according to Example VIII, supra, containing the compound having the structure:

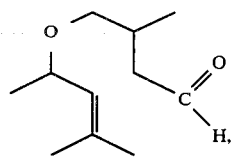

is added to the reaction mass over a period of two hours. During the addition of this material, the reaction mass temperature rises to 40° C. as a result of the exothermic reaction. The reaction mass is cooled and maintained at 40° C. with stirring for a period of four hours. At the end of the four hour period, the reaction mass is cooled to room temperature. A 5% aqueous solution of hydrochloric acid is added to the reaction mass. The reaction mass is then washed with water followed by a saturated sodium carbonate solution until neutral. The resulting reaction mass is then distilled on a 2″ splash column yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 83/ | 94/ | 1.6 | 3.0 |
| 2 | 81 | 86 | 1.3 | 4.0 |
| 3 | 81 | 86 | 1.3 | 5.1 |
| 4 | 90 | 96 | 2.2 | 2.5 |
| 5 | 90 | 110 | 2.0 | 10.0 |
| 6 | 94 | 210 | 2.0 | 5.9 |

FIG. 20 is the GLC profile for the crude reaction product containing the compound having the structure:

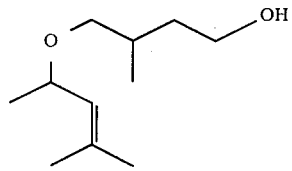

FIG. 21 is the NMR spectrum for fraction 4 of the foregoing distillation product containing the compound having the structure:

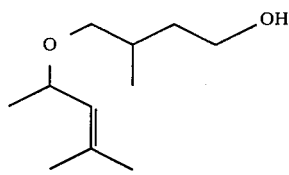

(Conditions: Field strength: 100 MHz; solvent: CFCl$_3$).

EXAMPLE X

PREPARATION OF 3-METHYL-4-PHENOXY-BUTANAL

Reaction:

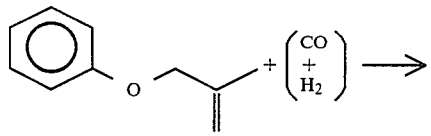

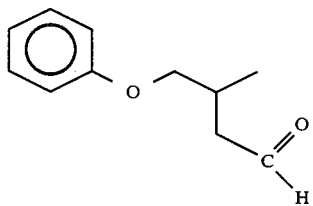

Into a high-pressure oxo-reactor are placed the following materials:

Allyl ether having the structure:

| | |
|---|---|
| (phenoxy allyl structure) | 148 grams (1 mole) |
| Triphenyl phosphine | 6 grams |
| Rhodium cholorol carbonyl (triphenyl phosphine) | 0.6 grams |

The oxo-reactor is sealed, heated to 140° C. and pressurized with a 50:50 mole:mole mixture of hydrogen and carbon monoxide. The reaction mass is stirred while maintaining the temperature of 140° C. and maintaining the pressure at 1000 psig for a period of ten hours.

At the end of the ten hour period, the oxo-reactor is cooled, opened and the contents removed and filtered.

The resulting filtrate is then distilled on a 2″ splash column yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 35/ | 45/ | 1.6 | 21.3 |
| 2 | 72 | 100 | 1.6 | 9.2 |
| 3 | 100 | 108 | 1.6 | 35.1 |
| 4 | 99 | 108 | 1.5 | 51.8 |
| 5 | 97 | 108 | 1.3 | 50.1 |
| 6 | 95 | 135 | 1.3 | 32.2 |

Fractions 2–6 are bulked and redistilled on a 12″ Goodloe column yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 50/58 | 112/117 | 2.8/3.0 | 6.6 |
| 2 | 62 | 112 | 1.6 | 10.0 |
| 3 | 94 | 127 | 1.6 | 12.7 |
| 4 | 94 | 128 | 1.5 | 14.2 |
| 5 | 88 | 128 | 1.2 | 12.1 |
| 6 | 88 | 128 | 1.2 | 13.0 |
| 7 | 100 | 128 | 1.2 | 8.4 |
| 8 | 104 | 127 | 2.3 | 10.4 |
| 9 | 100 | 128 | 2.0 | 17.9 |
| 10 | 104 | 131 | 2.3 | 18.0 |
| 11 | 102 | 147 | 2.3 | 14.8 |
| 12 | 80 | 100 | 2.3 | 8.9 |

FIG. 22A is the GLC profile for the crude reaction product containing the compound having the structure:

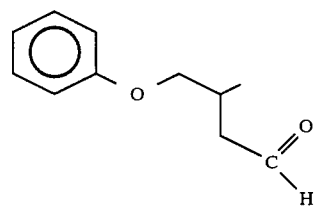

FIG. 22B is the NMR spectrum for the compound having the structure:

(Conditions: Solvent: CFCl$_3$; Field strength: 100 MHz).

EXAMPLE XI

PINE FRAGRANCE

The following pine fragrance formulations are prepared:

| | Parts By Weight | | |
|---|---|---|---|
| Ingredients | IX-A | IX-B | IX-C |
| Isobornyl acetate | 100 | 100 | 100 |

-continued

| Ingredients | Parts By Weight | | |
|---|---|---|---|
| | IX-A | IX-B | IX-C |
| Camphor | 10 | 10 | 10 |
| Terpineol | 25 | 25 | 25 |
| Fir balsam absolute (50% in diethyl phthalate) | 20 | 20 | 20 |
| Coumarin | 4 | 4 | 4 |
| Linalool | 30 | 30 | 30 |
| Frenchyl alcohol | 10 | 10 | 10 |
| Anethol | 12 | 12 | 12 |
| Lemon terpenes washed | 50 | 50 | 50 |
| Borneol | 5 | 5 | 5 |
| Galbanum oil | 5 | 5 | 5 |
| Turpentine Russian | 150 | 150 | 150 |
| Eucalyptol | 50 | 50 | 50 |
| 2,2,6-trimethyl-1-cyclohexene-1-carboxaldehyde | 12 | 12 | 12 |
| Maltol (1% in diethyl phthalate) | 5 | 5 | 5 |
| Compound having the structure: 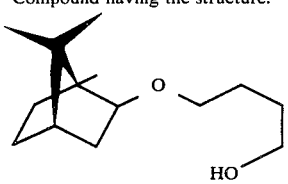 prepared according to Examples IV or V | 28 | 0 | 0 |
| Compound having the structure: 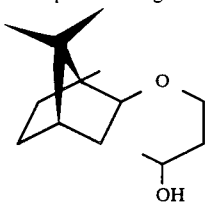 prepared according to Example VI | 0 | 28 | 0 |
| Compound having the structure: 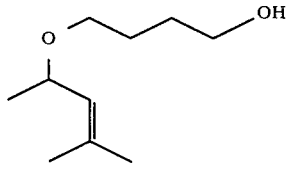 prepared according to Example IX | 0 | 0 | 28 |

The compound having the structure:

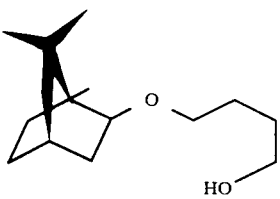

imparts to the pine formulation an intense minty patchouli aroma and causes it to have intense patchouli topnotes. Accordingly, the pine formulation can be described as "piney with an intense patchouli and minty aroma having patchouli topnotes".

The compound having the structure:

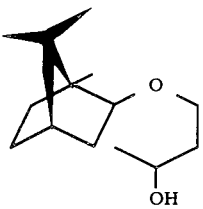

imparts to this piney formulation a very natural-like incense and cedarwood aroma. Accordingly, the formulation thus prepared can be described as "natural piney with cedarwood-like and incense topnotes".

The compound having the structure:

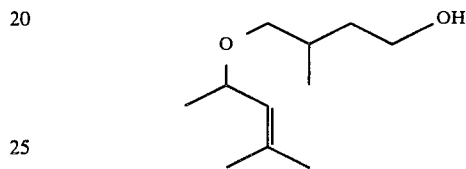

imparts to this piney formulation a camphoraceous, woody, lavender, spicy and floral aroma with patchouli and rosey undertones. Accordingly, the formulation can be described from a perfumery standpoint as "piney with camphoraceous woody, lavender, spicy, floral, patchouli and rosey undertones."

EXAMPLE XII

FLORAL PERFUME COMPOSITIONS

The compound having the structure:

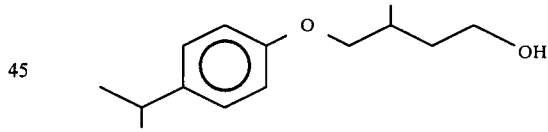

produced according to Example II has an ozoney fresh air dried cloth-like, green, orange, nutty and woody aroma. This material has great warmth and richness and blends well with many floral concepts. It is a rather unique floral note of great value to perfumery. Its use may be demonstrated by the following floral fragrance whereby the compound having the structure:

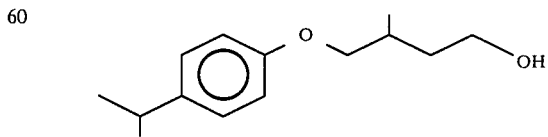

is used to the extent of 5% by weight.

The compound having the structure:

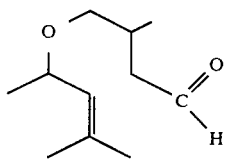

produced according to Example VIII imparts to this floral fragrance a herbaceous, strong green, leafy, peppery and spicy aroma with herbaceous, peppery, olibanum and diffusive amber-like undertones. The addition of 5% by weight of the compound having the structure:

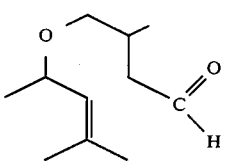

imparts a very desirable spicy and green character.

The compound having the structure:

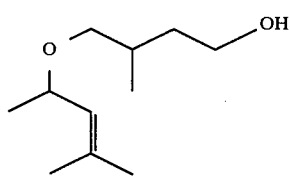

imparts to the floral formulation a camphoraceous, woody, lavender and spicy aroma.

The compound having the structure:

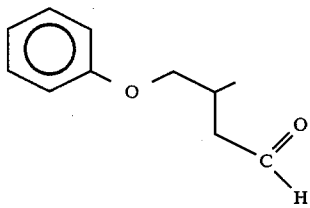

imparts to the floral formulation a herbaceous, sweet fruity, chamomile-like undertone.

All four of these products perform quite well in fragrances and are judged to be very valuable fragrance materials:

| FLORAL FRAGRANCE | "A" | "B" | "C" | "D" |
|---|---|---|---|---|
| Citronellol | 12.3 | 12.3 | 12.3 | 5.0 |
| Geraniol | 2.5 | 2.5 | 2.5 | 5.0 |
| Amyl Cinnamic Aldehyde | 24.6 | 24.6 | 24.6 | 5.0 |
| Galaxolide ® 50 (Trademark Tricyclic Isochroman of International Flavors & Fragrances Inc.) | 9.8 | 9.8 | 9.8 | 5.0 |
| Vertenex High Cis (Cis-t Butylcyclohexenyl Acetate; Para Isomer) | 7.4 | 7.4 | 7.4 | 5.0 |
| Rose Oxide | 0.7 | 0.7 | 0.7 | 5.0 |
| Cinnamic Alcohol | 19.6 | 19.6 | 19.6 | 5.0 |
| Aldehyde C-11 (n-Undecylenic Aldehyde) | 0.5 | 0.5 | 0.5 | 5.0 |
| Aldehyde C-12 (n-Dodecyl Aldehyde in 10% solution in diethyl phthalate) | 0.5 | 0.5 | 0.5 | 5.0 |
| Citronellal (10% solution in diethyl phthalate) | 0.5 | 0.5 | 0.5 | 5.0 |
| Phenyl Ehtyl Acetate | 2.5 | 2.5 | 2.5 | 5.0 |
| Ylang Oil | 1.2 | 1.2 | 1.2 | 5.0 |
| Indisan (Hydrogenated derivative of reaction product of Camphene and Resorcinol) | 3.7 | 3.7 | 3.7 | 5.0 |
| Musk Ketone | 5.0 | 5.0 | 5.0 | 5.0 |
| Oakmoss Resin | 0.5 | 0.5 | 0.5 | 5.0 |
| Liatrix Absolute (10% in diethyl phthalate) | 2.5 | 2.5 | 2.5 | 5.0 |
| Vetiver Acetate | 1.2 | 1.2 | 1.2 | 5.0 |
| Diethyl Phthalate | 5.0 | 5.0 | 5.0 | 5.0 |
| Compound having the structure: 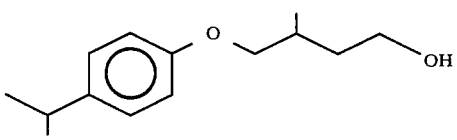 produced according to Example II. | 5.0 | 0 | 0 | 0 |
| Compound having the structure: (structure shown) | 0 | 5.0 | 0 | 0 |
| Compound having the structure: (structure shown) | 0 | 0 | 5.0 | 0 |
| Compound having the structure: (structure shown) | 0 | 0 | 0 | 5.0 |

Thus, as a result of adding the compound having the structure:

the fragrance can be described as "floral with ozoney, fresh air dried cloth-like, green and fresh orange undertones".

The fragrance produced by having the compound having the structure:

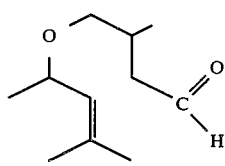

added thereto, can be described as "floral with herbaceous strong green, leafy, pepper, spicy, olibanum and diffusive amber undertones".

The fragrance produced by having added thereto the compound having the structure:

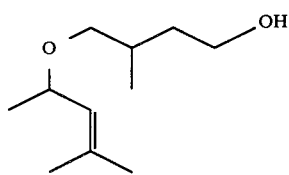

can be described as "floral with camphoraceous, woody, lavender, spicy, patchouli and rosey undertones".

The fragrance having added thereto the compound having the structure:

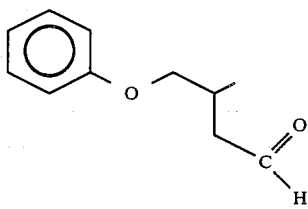

can be described as "floral with herbaceous, sweet fruity, chamomile-like and caramellic undertones".

EXAMPLE XIII

PREPARATION OF LILAC FRAGRANCE

The following mixture is prepared:

| | |
|---|---|
| Hydroxycitronellal | 22% |
| Phenyl Ethyl Alcohol | 12% |
| Heliotropine | 12% |
| Linalool | 8% |
| Cinnamic Alcohol | 4% |
| Indole - 10% in Diethyl Phthalate | 2% |
| Benzyl Acetate | 8% |
| Anisic Alcohol | 8% |
| Coumarin - 10% in Diethyl Phthalate | 4% |
| Compound having the structure: 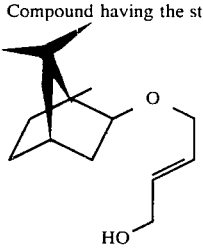 prepared according to Example VII. | 4% |

The compound having the structure:

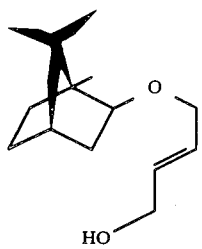

imparts to this lilac fragrance an interesting animalic sweaty lavender-like undertone. Accordingly, the fragrance can be described as "lilac with an animalic sweaty lavender-like undertone".

EXAMPLE XIV

PREPARATION OF COSMETIC POWDER COMPOSITIONS

Cosmetic powder compositions are prepared by mixing in a ball mill 100 grams of talcum powder with 0.25 grams of each of the substances set forth in Table III below. Each of the cosmetic powder compositions has an excellent aroma as described in Table III below:

TABLE III

| SUBSTANCE | AROMA DESCRIPTION |
|---|---|
| Compound having the structure ![structure] produced according to Example II. | A nutty, woody, ozoney, fresh air dried cloth, green, orange aroma profile. |
| Compound having the structure: ![structure] produced according to Example IV or V | A minty patchouli aroma with patchouli undertones. |
| Compound having the structure: ![structure] prepared according to Example VI | An incense aroma with cedarwood undertones. |
| Compound having the structure: ![structure] | An onion, garlic and lavender aroma profile with oniony, animalic sweaty undertones. |

TABLE III-continued

| SUBSTANCE | AROMA DESCRIPTION |
|---|---|
| Compound having the structure: 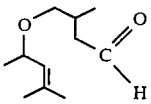 prepared according to Example VIII | A herbaceous, strong green leafy, pepper and spicy aroma with herbaceous peppery olibanum and diffusive amber undertones. |
| Compound having the structure: 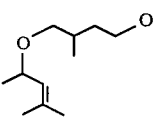 produced according to Example IX | A camphoraceous, woody, lavender, spicy and floral aroma with patchouli and rosey undertones. |
| Compound having the structure: 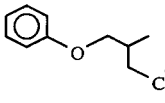 prepared according to Example X | A herbaceous, sweet fruity, and chamomile-like aroma with caramellic undertones. |
| Fragrance of Example XI(A). | A piney aroma with an intense patchouli and minty aroma having patchouli topnotes. |
| Fragrance of Example XI(B). | A natural piney aroma with cedarwood-like and incense topnotes. |
| Fragrance of Example XI(C). | A piney aroma with camphoraceous, woody, lavender, spicy, floral patchouli and rosey undertones. |
| Perfume composition of Example XII(A). | Floral with ozoney, fresh air dried cloth-like, green and orange undertones. |
| Perfume composition of Example XII(B) | Floral with herbaceous, strong green, leafy, peppery, spicy, olibanum and diffusive amber undertones. |
| Perfume composition of Example XII(C) | Floral with camphoraceous, woody, lavender, spicy, patchouli and rosey undertones. |
| Perfume composition of Example XII(D) | Floral with herbaceous, sweety fruity, chamomile-like and caramellic undertones. |
| Perfume composition of Example XIII | Lilac with an animalic, sweaty, lavender-like undertones. |

EXAMPLE XV

PERFUMED LIQUID DETERGENT

Concentrated liquid detergents with aromas as set forth in Table III of Example XIV (which detergents are prepared from Lysine salt of n-dodecyl benzene sulfonic acid as more specifically described in U.S. patent, Ser. No. 3,948,818 issued on Apr. 6, 1976 the specification for which is incorporated by reference herein) are prepared containing each of the substances set forth in Table III of Example XIV, supra. They are prepared by adding and homogeneously mixing the appropriate quantity of perfumery substance as set forth in Table III of Example XIV in the liquid detergent. The detergents all possess aromas as set forth in Table III of Example XIV, the intensity increasing with greater concentrations of perfumery substance of Table III of Example XIV, supra.

EXAMPLE XVI

PREPARATION OF A COLOGNE AND HANDKERCHIEF PERFUME

The perfume substances of Table III of Example XIV, supra, are incorporated into colognes at concentrations of 1.5%, 2.0%, 2.5%, 3.0% and 4.0% in 80%, 85% and 90% aqueous ethanols; and into a handkerchief perfume composition at concentrations of 10%, 15%, 20%, 25% and 30% (in 85%, 90% and 95% aqueous ethanols). Distinct and definitive aromas as set forth in Table III of Example XIV are imparted to the cologne and to the handkerchief perfume compositions.

EXAMPLE XVII

PREPARATION OF A DETERGENT COMPOSITION

A total of 100 grams of a detergent powder (a nonionic detergent powder containing a proteolytic enzyme prepared according to Example I of Canadian Pat. No. 985,190 issued on Mar. 9, 1976 the disclosure of which is incorporated by reference herein) is mixed with 0.15 grams of each of the substances set forth in Table III of Example XIV, supra, until substantially homogeneous compositions are obtained. These compositions have excellent aromas as set forth in Table III of Example XIV.

EXAMPLE XVIII

PREPARATION OF SOAP

Each of the perfumery substances of Table III of Example XIV are incorporated into soap (LVU-1) at 0.1% by weight of each substance. After two weeks in the oven at 90° F. each of the soaps showed no visual effect from the heat. Each of the soaps manifested an excellent aroma as set forth in Table III of Example XIV, supra.

EXAMPLE XIX

PREPARATION OF SOAP COMPOSITION

One hundred grams of soap chips (IVORY ®, registered trademark of the Procter & Gamble Co. of Cincinnati, Ohio) are mixed individually with one gram each of the perfumery substances of Table III of Example XIV, supra, until a homogeneous composition is obtained. The homogeneous composition is then treated under three atmospheres pressure at 180° C. for a period of three hours and the resulting liquid is placed into a soap mold. The resulting soap cakes, on cooling, manifest excellent aromas as set forth in Table III of Example XIV, supra.

EXAMPLE XX

PREPARATION OF A SOLID DETERGENT COMPOSITION

A detergent is prepared from the following ingredients according to Example I of Canadian Pat. No. 1,007,948 the specification for which is incorporated by reference herein:

| Ingredients | Parts by Weight |
| --- | --- |
| "Neodol 45-11" (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed separately with 0.15 grams of each of the perfume substances of Table III of Example XIV, supra. The detergent samples each have excellent aromas as set forth in Table III of Example XIV, supra.

EXAMPLE XXI

Utilizing the procedure of Example I at column 15 of U.S. Pat. No. 3,632,396 (the specification for which is incorporated by reference herein), a non-woven cloth substrate useful as a dryer-added fabric softening article of manufacture is prepared, wherein the substrate, the substrate coating and the outer coating and the perfuming material are as follows:
1. a water "dissolvable" paper ("Dissolvo Paper")'
2. Adogen 448 (m.p. about 140° F.) as the substrate coating; and
3. an outer coating having the following formulation (m.p. about 150° F.);
   57 percent $C_{20-22}$HAPS
   22 percent isopropyl alcohol
   20 percent antistatic agent
   1 percent of one of the perfume substances of of Table III of Example XIV, supra.

A fabric softening composition prepared as set forth above having the above aroma characteristics as set forth in Table III of Example XIV, supra, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth in Table III of Example XIV is imparted in a pleasant manner to the headspace in the dryer on operation thereof, using said dryer-added fabric softening non-woven fabric.

EXAMPLE XXII

FLAVOR COMPOSITION

The following basic walnut flavor formulation is prepared:

| INGREDIENTS | PARTS BY WEIGHT |
| --- | --- |
| Ethyl-2-Methyl Butyrate | 10 |
| Vanillin | 40 |
| Butyl Valerate | 40 |
| 2,3-Diethyl Pyrazine | 5 |
| Methyl Cyclopentenolone | 80 |
| Benzaldehyde | 60 |
| Valerian Oil Indian (1% in 95% aqueous ethanol alcohol) | 0.5 |
| Propylene Glycol | 764.5 |

The compound having the structure:

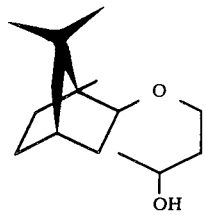

prepared according to the process of Example VI is added to the above formulation at the rate of 1.5%. The formulation is compared to a formulation which does not have the compound having the structure:

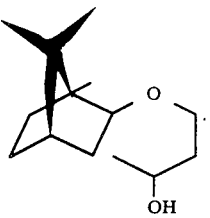

The formulation containing the compound having the structure:

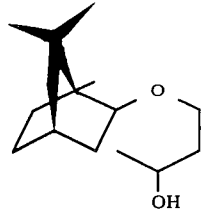

has a woody-balsamic, fresh walnut kernel and walnut skin-like taste and, in addition, has a fuller mouth-feel and longer lasting taste. The flavor that has added to it, the compound having the structure:

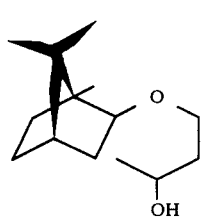

is preferred by a group of flavor panelists not associated with the assignee of the instant application of the inventorship entity and they consider it to be a substantially improved walnut flavor.

EXAMPLE XXIII

ORANGE FLAVOR FORMULATION

An orange flavor formulation is prepared by admixing:

| INGREDIENTS | PARTS BY WEIGHT |
| --- | --- |
| Natural orange oil | 13.00 |
| Acetaldehyde | 1.50 |
| Ethyl acetate | 0.10 |
| Ethyl butyrate | 0.50 |
| Propanol | 0.10 |
| trans-2-Hexenal | 0.10 |

| INGREDIENTS | PARTS BY WEIGHT |
| --- | --- |
| Ethyl alcohol (95%) | 60.00 |
| Fusel oil | 0.05 |
| Propylene glycol | 24.65 |

This is denominated Flavor A. A second formulation, Flavor B is prepared by adding the compound having the structure:

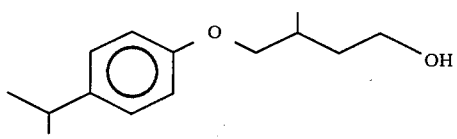

prepared according to Example II to a portion of Flavor A and the ration of two parts to 100 parts of Flavor A.

Each of Flavors A and B is added in the amount of 2 ounces per gallon of 32° Baume sugar syrup to produce a syrup for combination with water to form a drink. The beverage prepared using Flavor A is a passable orange beverage of good character, flavor and intensity.

The beverage prepared using Flavor B has a much improved flavor. The improvement contributed by the compound having the structure:

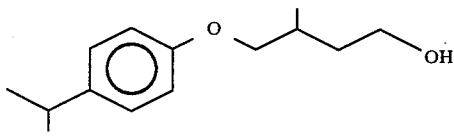

is due to:
i. a greater degree of natural character of freshly squeezed orange juice
ii. an increase in the pulplike notes and
iii. greater orange juice flavor depth.

EXAMPLE XXIV 0.5 Grams of the mixture:

| INGREDIENTS | PARTS BY WEIGHT |
| --- | --- |
| Dimethyl sulfide | 4 |
| Methyl propyl disulfide | 25 |
| Methyl propenyl disulfide | 2 |
| Dipropyl disulfide | 12 |
| Propyl propenyl disulfide | 8 |
| Diallyl disulfide | 1 |
| Compound having the structure | 12 | prepared according to Example VII is imulsified in a solution containing the following materials:
100 grams gum arabic
300 grams water
0.5 grams 20 percent solution in ethanol of butylated hydroxy anisole.

The resultant emulsion is spray-dried in a Bowen Lab. Model spray-drier, inlet temperature 500° F., outlet temperature 200° F. 12 Grams of this spray-dried material is mixed with 29.2 grams of the following soup base:

| INGREDIENTS | PARTS BY WEIGHT |
| --- | --- |
| Fine ground sodium chloride | 35.62 |
| Hydrolized vegetable protein [4 BE:Nestle's] | 27.40 |
| Mono sodium glutamate | 17.81 |
| Mono calcium glutamate | 17.81 |
| Sucrose | 10.96 |
| Beef Fat | 5.48 |
| Sethness caramel color [powder B & C] | 2.73 |

The resultant mixture is then added to 12 ounces of boiling water and an excellent onion-flavored soup is obtained which is comparative to that created using natural onions or natural onion oil.

EXAMPLE XXV

TOOTHPASTE

The compound having the structure:

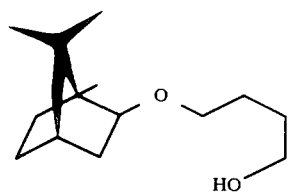

prepared according to Example IV or V is incorporated at the rate of 0.1% in toothpaste (Colgate MFP Fluoride Gel "Winterfresh" manufactured by the Colgate Palmolive Corporation of New York, N.Y.) and evaluated by a panel of nine people for its aroma characteristics against a control without the addition of the compound having the structure:

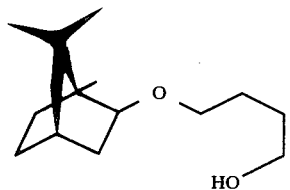

The entire panel unanimously preferred the toothpaste with the compound having the structure:

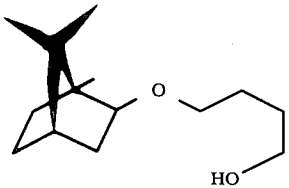

as having a fresher, more cooling aroma with patchouli overtones and oriental, incense, musky and sandalwood nuances than the control.

A small group of panelists (3 in number) brushed their teeth with the same toothpaste using 0.1%, 0.2% and 0.5% of the compound having the structure:

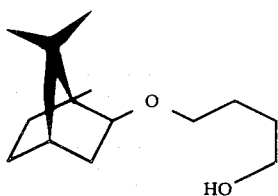

produced according to Example III or IV brushing their teeth at three hour intervals. All members of the panel are of the opinion that the clean, fresh sensation lasted longer with the toothpaste containing the compound having the structure:

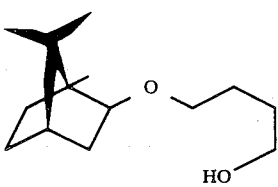

than without it. In addition, all members of the panel state that the bitter after-taste related to the saccharin in the toothpaste is depressed and a more pleasant after-taste is created. No off-note is created by the compound having the structure:

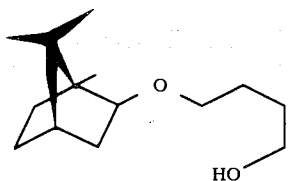

In addition, when the compound having the structure:

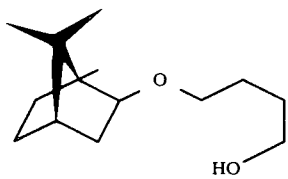

is used at a level 0.5% the same results are obtained with no off-note created by the compound having the structure:

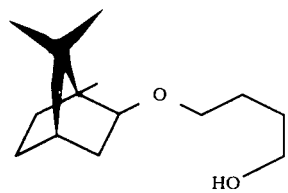

Therefore, it is concluded that the compound having the structure:

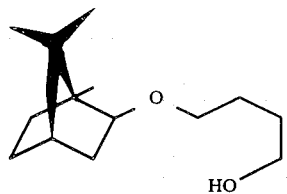

is effective in improving oral hygiene products including toothpaste, mouthwash, mouth sprays and sugar-based tablets and in addition, chewing gum.

The compound having the structure:

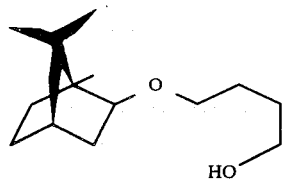

improves the organoleptic properties of toothpaste, chewing gum, mouthwash, mouth sprays and sugar-based mouth freshener tablets:
(i) by adding fresher topnotes
(ii) by enhancing the menthol-like cooling notes (without using menthol)
(iii) by extending the fresh after-taste without having an effect similar to that of chloroform (without the use of chloroform), and
(iv) by imparting oriental incense, musky and sandalwood and patchouli nuances to the toothpaste.

The foregoing effects are unexpected, unobvious and advantageous.

EXAMPLE XXVI(A)

FLAVOR PREPARATION

The following flavor formulation is prepared by admixing the ingredients in the proportion set forth below:

| Ingredients | Parts by Weight |
|---|---|
| Clove oil | 1.0 |
| Cardamom oil | 0.1 |
| Spearmint oil | 5.0 |
| Anethol | 2.0 |
| Compound having the structure:<br>produced according to Examples IV or V. | 4.0 |
| Peppermint oil, redistilled | 83.9 |
| Prenyl methyl carbonate | 2.0 |

EXAMPLE XXVI(B)

Ten parts by weight of 50 Bloom pigskin gelatin is added to ninety parts by weight of water at a temperature of 150° F. The mixture is agitated until the gelatin completely dissolves and the solution is cooled to 120° F. Twenty parts by weight of the flavor of Part (A) supra is added to the solution which is then homogenized to form an emulsion, having a particle size typically in the range of 2-5 microns. The material is kept at 120° F. under which conditions the gelatin will not gel.

Coacervation is induced by adding, slowly and uniformly 40 parts by weight of a 20% aqueous solution of sodium sulfate. During coacervation, the gelatin molecules are deposited uniformly about each oil droplet as a nucleus.

Gelation is effected by pouring the heated coacervate mixture into 1,000 parts by weight of a 7% aqueous solution of sodium sulfate at 65° F. The resulting jelled coacervate may be filtered and washed with water at temperatures below the melting point of gelatin to remove the salt.

Hardening of the filtered cake, in this example, is effected by washing with 200 parts by weight of 37% solution of formaldehyde in water. The cake is then washed to remove residual formaldehyde.

EXAMPLE XXVI(C)

The following mixture is prepared:

| Ingredients | Parts by Weight |
| --- | --- |
| Liquid flavor composition of Part (A) supra | 48.4 |
| Cab-O-Sil M-5 (brand of silica produced by the Cabot Corporation of 125 High Street, Boston, Mass. 02110 Physical properties: Surface Area: 200 m²/gm. Nominal particle size: 0.012 microns Density: 2.3 lbs/cu. ft. | 3.2 |

The Cab-O-Sil is dispersed in the liquid flavor composition of Part (A) with vigorous stirring thereby resulting in a viscous liquid. 48.4 parts by weight of the powder flavor composition produced according to Part (B) supra, is then blended into said viscous liquid with stirring at 25° C. for a period of 30 minutes resulting in a thixotropic sustained release patchouli-like and incense/ethereal/"cooling effect" flavored composition.

EXAMPLE XXVII

CHEWING GUM

One hundred parts by weight of chicle are mixed with four parts by weight of the flavor prepared in accordance with Example XXVI. Three hundred parts of sucrose and one hundred parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long-lasting, patchouli-like and incense/cooling/freshening flavor.

EXAMPLE XXVIII

TOOTHPASTE FORMULATION

The following separate groups of ingredients are prepared:

| Ingredient | Parts by Weight |
| --- | --- |
| Group "A" | |
| Glycerine | 30.200 |
| Distilled water | 15.325 |
| Sodium benzoate | 0.100 |
| Saccharin sodium | 0.125 |
| Stannous fluoride | 0.400 |
| Group "B" | |
| Calcium carbonate | 12.500 |
| Dicalcium phosphate (dihydrate) | 37.200 |
| Group "C" | |
| Sodium N—lauroyl sarcosinate (foaming agent) | 2.000 |
| Group "D" | |
| Flavor materials of Example XXVI | 1.200 |

Procedure:

1. The ingredients in Group "A" are stirred and heated in a steam jacketed kettle to 160° F.
2. Stirring is continued for an additional three to five minutes to form a homogenous gel.
3. The powders of Group "B" are added to the gel while mixing until a homogenous paste is formed.
4. With stirring, the flavor of "D" is added and lastly the sodium n-lauroyl sarcosinate.
5. The resultant slurry is then blended for one hour. The completed paste is then transferred to a three roller mill and then homogenized and finally tubed.

The resulting toothpaste when used in a normal tooth-brushing procedure yields a pleasant patchouli-like and incense/cooling/freshening flavor of constant strong intensity throughout said procedure (1-1.5 minutes).

EXAMPLE XXIX

TOBACCO FLAVOR FORMULATION

Cigarettes are produced using the following tobacco formulation:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| H₂O | 5.3 |

At the rate of 0.2%, the following tobacco flavor formulation is applied to all of the cigarettes produced with the above tobacco formulation.

| Ingredients | Parts by Weight |
| --- | --- |
| Ethyl Butyrate | .05 |
| Ethyl Valerate | .05 |
| Maltol | 2.00 |
| Cocoa Extract | 26.00 |
| Coffee Extract | 10.00 |
| Ethyl Alcohol (95%) | 20.00 |
| H₂O | 41.90 |

To 50% of the cigarettes, 10 and 20 ppm of the compound having the structure:

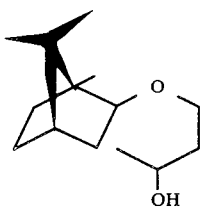

are added. These cigarettes are hereinafter called "experimental" cigarettes and the cigarettes without the compound having the structure:

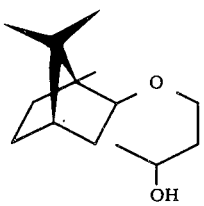

produced according to Example VI are hereinafter called "control" cigarettes. The control and experimental cigarettes are then evaluated by paired comparison and the results are as follows:

a. In aroma, the experimental cigarettes are found to be more aromatic with a woody, incense, oriental and patchouli aroma and taste.

b. In smoke flavor, the experimental cigarettes are found aromatic, more sweet, more bitter, richer and slightly less harsh in the mouth and more cigarette tobacco-like than the control cigarettes with woody, incense, oriental and patchouli-like aroma and taste nuances.

In summary, the experimental cigarettes containing 20 ppm is the compound having the structure:

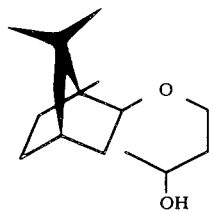

produced according to Example VI are found to be woody, incense, oriental and patchouli-like and turkish tobacco-like in the main stream and in the side stream.

All cigarettes both control and experimental are evaluated for smoke flavor with 20 mm cellulose acetate filters.

A similar effect occurs when using the compound having the structure:

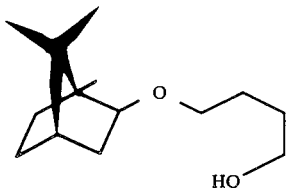

produced according Examples IV or V.

What is claimed is:

1. The ether carbinol having the structure:

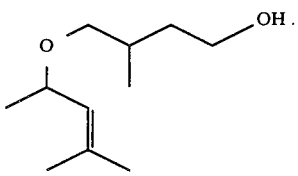

* * * * *